(12) United States Patent
Yamakawa et al.

(10) Patent No.: US 7,115,699 B2
(45) Date of Patent: Oct. 3, 2006

(54) SULFONATED POLYMER HAVING NITRILE-CONTAINING HYDROPHOBIC BLOCK AND SOLID POLYMER ELECTROLYTE

(75) Inventors: Yoshitaka Yamakawa, Tokyo (JP); Makoto Higami, Tokyo (JP); Toshiaki Kadota, Tokyo (JP)

(73) Assignee: JSR Corporation, Tokyo (JP)

( * ) Notice: Subject to any disclaimer, the term of this patent is extended or adjusted under 35 U.S.C. 154(b) by 167 days.

(21) Appl. No.: 10/958,622

(22) Filed: Oct. 6, 2004

(65) Prior Publication Data

US 2005/0080220 A1   Apr. 14, 2005

(30) Foreign Application Priority Data

Oct. 7, 2003 (JP) ............................. 2003-348524

(51) Int. Cl.
*C08G 75/00* (2006.01)
*C08G 65/38* (2006.01)
*C08G 67/00* (2006.01)

(52) U.S. Cl. ...................... 528/172; 528/171; 528/174; 528/175; 528/86; 528/373; 525/242; 525/291; 525/293; 525/294

(58) Field of Classification Search .............. 528/172, 528/171, 174, 175, 86, 373; 525/242, 291, 525/293, 294
See application file for complete search history.

(56) References Cited

FOREIGN PATENT DOCUMENTS

EP   1 245 555 A1   10/2002
EP   1 329 444 A1   7/2003

Primary Examiner—Duc Truong

(74) Attorney, Agent, or Firm—Oblon, Spivak, McClelland, Maier & Neustadt, P.C.

(57) ABSTRACT

Provided are a sulfonated polymer capable of high hot water resistance even if it has an increased amount of the sulfonic groups introduced therein, and a solid polymer electrolyte containing the sulfonated polymer that has high proton conductivity and excellent generating performance.

The sulfonated polymer has repeating units represented by the formula (1'):

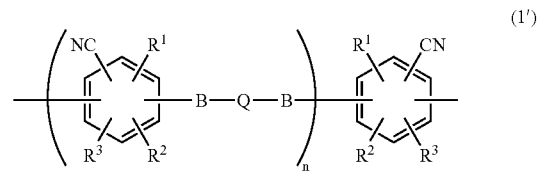

(1')

wherein B's are each independently an oxygen or a sulfur atom, $R^1$ to $R^3$ may be the same or different and are selected from a hydrogen atom, a fluorine atom, a nitrile group and an alkyl group, n is an integer of 2 or greater, and Q is a structure represented by the formula (q):

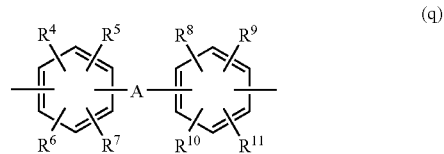

(q)

wherein A is independently a divalent atom or organic group or a direct bond, and $R^4$ to $R^{11}$ may be the same or different and are selected from a hydrogen atom, a fluorine atom, an alkyl group and an aromatic group.

13 Claims, 8 Drawing Sheets

SULFONATED POLYMER HAVING NITRILE-CONTAINING HYDROPHOBIC BLOCK AND SOLID POLYMER ELECTROLYTE

FIELD OF THE INVENTION

The present invention relates to a compound having nitrile groups, a sulfonated polymer containing repeating units derived from the compound, and a solid polymer electrolyte comprising the sulfonated polymer.

BACKGROUND OF THE INVENTION

Recently, solid electrolytes are used more often than the conventional electrolyte (aqueous) solutions. This is because firstly those solid electrolytes have good processability in application in electric and electronic components, and secondly there are trends for overall size and weight reduction of such components and further for power saving.

Proton conductive materials, both inorganic and organic, are known in the art. However, inorganic proton conductive compounds, such as uranyl phosphate hydrate, come with many difficulties when superposed as a conductive layer onto a substrate or an electrode. For example, sufficient contact cannot be achieved in the interface between the conductive layer and the substrate or the like.

On the other hand, the organic proton conductive compounds include organic polymers that belong to the so-called cation exchange resins, for example sulfonated vinyl polymers such as polystyrene sulfonic acid; perfluoroalkylcarboxylic acid polymers and perfluoroalkylsulfonic acid polymers represented by Nafion® (DuPont); and polymers occurring by introducing sulfonic or phosphoric groups in heat resistant polymers such as polybenzimidazole and polyether ether ketone (Polymer Preprints, Japan, Vol. 42, No. 7, p. 2490–2492 (1993), Polymer Preprints, Japan, Vol. 43, No. 3, p. 735–736 (1994), Polymer Preprints, Japan, Vol. 42, No. 3, p. 730 (1993)).

These organic polymers are generally in the form of film when used as electrolytes. Their solvent solubility and thermoplasticity enable them to form a conductive membrane jointly on an electrode. However, many of the organic polymers are still insufficient in proton conductivity. In addition, they have poor service durability, reduce proton conductivity at high temperatures (100° C. or above), are embrittled by sulfonation to cause low mechanical strength, and have high moisture dependence. Moreover, the adhesion thereof with an electrode is not satisfactorily good. Further, because of the water-containing structure of these polymers, the conductive membranes are excessively swollen during operation, resulting in lowered strength and deformation.

U.S. Pat. No. 5,403,675 discloses a solid polymer electrolyte comprising a sulfonated rigid-rod polyphenylene. This polymer mainly contains an aromatic compound composed of phenylene units and has been sulfonated by reaction with a sulfonating agent to introduce therein sulfonic groups. Although increasing the amount of the sulfonic groups introduced improves the proton conductivity, it also results in remarkably deteriorated hot water resistance and toughness.

OBJECTS OF THE INVENTION

It is an object of the invention to provide a sulfonated polymer capable of high hot water resistance even if it has an increased amount of the sulfonic groups introduced therein. The invention has another object of providing a solid polymer electrolyte comprising the sulfonated polymer that has high proton conductivity and excellent generating performance.

DISCLOSURE OF THE INVENTION

To achieve the above objects, the invention provides a novel compound having nitrile groups, a sulfonated polyarylene containing hydrophobic repeating units (hereinafter hydrophobic units) derived from the novel compound and repeating units having a sulfonic group, and a solid polymer electrolyte comprising the sulfonated polyarylene, as described below:

(1) A compound represented by the formula (1):

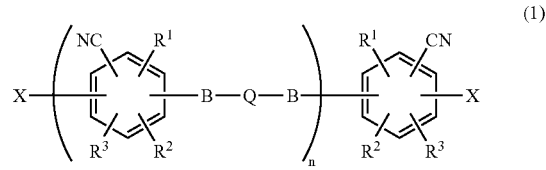

wherein B's are each independently an oxygen or a sulfur atom, X's are each an atom or a group selected from halogen atoms other than fluorine, —OSO$_2$CH$_3$ and —OSO$_2$CF$_3$, R$^1$ to R$^3$ may be the same or different and are selected from a hydrogen atom, a fluorine atom, a nitrile group and an alkyl group, n is an integer of 2 or greater, and Q is a structure represented by the formula (q):

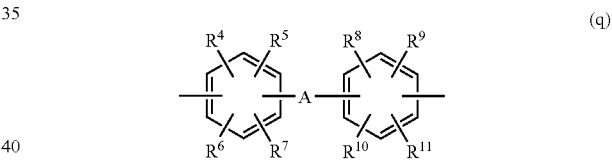

wherein A is independently a divalent atom or organic group or a direct bond, and R$^4$ to R$^{11}$ may be the same or different and are selected from a hydrogen atom, a fluorine atom, an alkyl group and an aromatic group.

(2) The compound as described in (1), wherein A in the structure represented by the formula (q) is a direct bond or an organic group selected from —CONH—, —(CF$_2$)$_p$— (wherein p is an integer of 1 to 10), —C(CF$_3$)$_2$—, —COO—, —SO—, —SO$_2$— and a group represented by the formula (a):

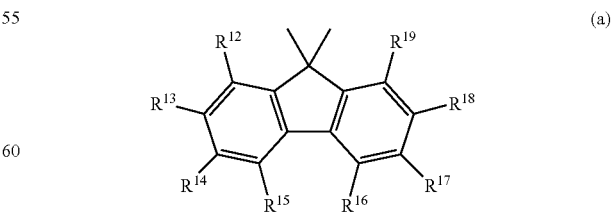

wherein R$^{12}$ to R$^{19}$ may be the same or different and are each a hydrogen atom, a fluorine atom, an alkyl group or an aromatic group.

(3) The compound as described in (1), comprising a structure (Q1) represented by the formula (q) in which A is an organic group selected from —CONH—, —(CF$_2$)$_p$— (wherein p is an integer of 1 to 10), —C(CF$_3$)$_2$—, —COO—, —SO— and —SO$_2$—, and a structure (Q2) of the same formula in which A is a direct bond or a group represented by the formula (a).

(4) The compound as described in (3), wherein the structure (Q1) accounts for 99 to 20 mol % and the structure (Q2) accounts for 1 to 80 mol % (with the proviso that the total of the structures (Q1) and (Q2) is 100 mol %).

(5) A polyarylene polymer comprising repeating units represented by the formula (1'):

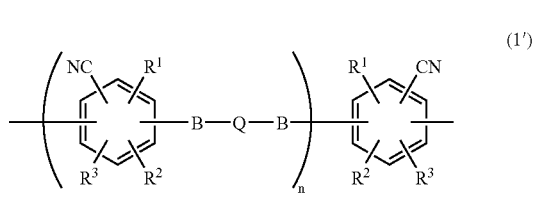

(1')

wherein B's are each independently an oxygen or a sulfur atom, R$^1$ to R$^3$ may be the same or different and are selected from a hydrogen atom, a fluorine atom, a nitrile group and an alkyl group, n is an integer of 2 or greater, and Q is a structure represented by the formula (q).

(6) The polyarylene polymer as described in (5), comprising repeating units of the formula (2) shown below:

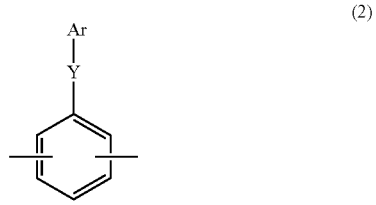

(2)

wherein Y is a divalent atom or organic group or a direct bond, and Ar is an aromatic group.

(7) The polyarylene polymer as described in (6), wherein the repeating units of the formula (2) have a sulfonate group.

(8) The polyarylene polymer as described in (6), wherein the repeating units of the formula (2) have a sulfonic group.

(9) A solid polymer electrolyte comprising the polyarylene polymer having a sulfonic group described in (8).

(10) A proton conductive membrane comprising the polyarylene polymer having a sulfonic group described in (8).

EFFECTS OF THE INVENTION

The sulfonated polymers with nitrile-containing hydrophobic units according to the present invention have excellent hot water resistance and high sulfonic acid concentration, so that they can produce solid polymer electrolytes capable of high proton conductivity and generating performance.

PREFERRED EMBODIMENTS OF THE INVENTION

Figure 1:
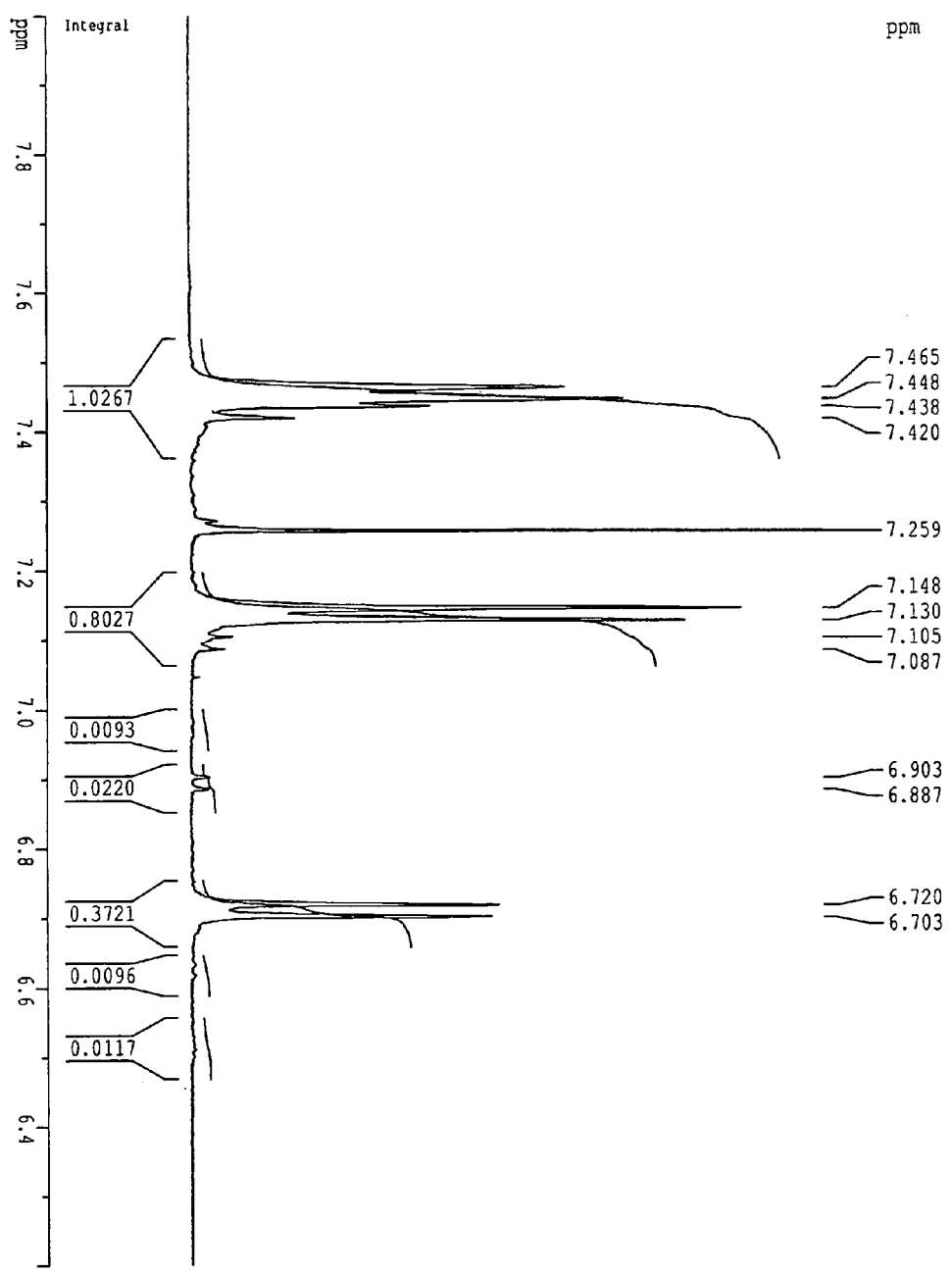
FIG. 1 is an NMR spectrum of the hydrophobic unit obtained in Example 1.

Hereinbelow, the compound with nitrile groups, the polyarylene polymer, the polyarylene polymer with sulfonic groups, the solid polymer electrolyte and the proton conductive membrane of the present invention will be described in detail.

(Compound with Nitrile Groups)

The compound of the formula (1), when contained as a monomer unit in a polymer, constitutes a hydrophobic block in the polymer and functions to enhance polymer's toughness and other mechanical strength properties because of its flexible structure.

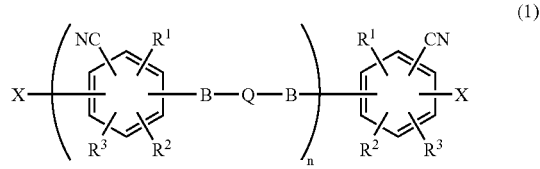

(1)

In the above formula, X's are each an atom or a group selected from halogen atoms other than fluorine (i.e., chlorine, bromine and iodine), —OSO$_2$CH$_3$ and —OSO$_2$CF$_3$.

R$^1$ to R$^3$ may be the same or different and are selected from a hydrogen atom, a fluorine atom, a nitrile group and an alkyl group.

Exemplary alkyl groups include methyl, ethyl, propyl, butyl, amyl and hexyl groups, with the methyl and ethyl groups being preferable.

B's are each independently an oxygen or a sulfur atom.

n is an integer of 2 or greater, and is generally up to 100, and preferably up to 80.

Q is a structure represented by the formula (q):

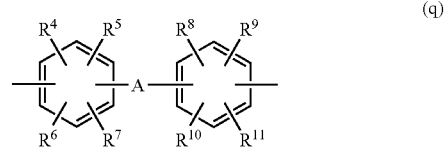

(q)

wherein R$^4$ to R$^{11}$ may be the same or different and are selected from a hydrogen atom, a fluorine atom, an alkyl group and an aromatic group. The alkyl groups include methyl, ethyl, propyl, butyl, amyl and hexyl groups, with the methyl and ethyl groups being preferable. The aromatic groups include phenyl, naphthyl, pyridyl, phenoxy diphenyl, phenyl phenyl and naphthoxy phenyl groups.

A is independently a divalent atom or organic group, or a direct bond. Examples thereof include electron-attracting groups such as —CO—, —CONH—, —(CF$_2$)$_p$— (where p is an integer of 1 to 10), —C(CF$_3$)$_2$—, —COO—, —SO— and —SO$_2$—, and electron-donating groups such as —O—, —S—, —CH=CH—, —C≡C— and groups represented by:

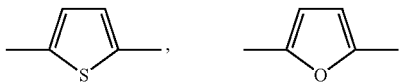

The electron-attracting group is defined as having a Hammett substituent constant of not less than 0.06 at the m-position and not less than 0.01 at the p-position of the phenyl group.

Examples of the group A further include those of the formula (a):

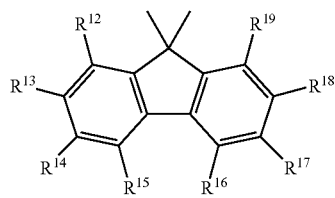

wherein R$^{12}$ to R$^{19}$ may be the same or different and are each a hydrogen atom, a fluorine atom, an alkyl group or an aromatic group. Examples of the alkyl and aromatic groups include those listed for R$^4$ to R$^{11}$.

The group A described above is preferably a direct bond or an organic group selected from —CONH—, —(CF$_2$)$_p$— (wherein p is an integer of 1 to 10), —C(CF$_3$)$_2$—, —COO—, —SO—, —SO$_2$—, and a group of the formula (a).

Exemplary compounds of the formula (1) include those having the structure Q which contains a structure (Q1) in which A is selected from —CONH—, —(CF$_2$)$_p$— (wherein p is an integer of 1 to 10), —C(CF$_3$)$_2$—, —COO—, —SO— and —SO$_2$—, and a structure (Q2) in which A is a direct bond or a group represented by the formula (a).

In particular, the structure (Q1) accounts for 99 to 20 mol %, preferably 95 to 30 mol %, and particularly preferably 90 to 35 mol %, and the structure (Q2) accounts for 1 to 80 mol %, preferably 5 to 70 mol %, and particularly preferably 10 to 65 mol % (with the proviso that the total of the structures (Q1) and (Q2) is 100 mol %). This proportion leads to smaller dimensional change of the polymer formed.

For example, the compound of the formula (1) may be synthesized by the following reactions:

First, an alkali metal such as lithium, sodium or potassium, or an alkali metal compound such as an alkali metal hydride, an alkali metal hydroxide or an alkali metal carbonate, is added to bisphenols combined together by a divalent atom or organic group or a direct bond thereby to convert them into a corresponding alkali metal salt of bisphenol. This reaction is made in a polar solvent of high dielectric constant, such as N-methyl-2-pyrrolidone, N,N-dimethylacetamide, sulfolane, diphenyl sulfone or dimethyl sulfoxide. The alkali metal or the like will be generally used in slight excess over the hydroxyl groups of the bisphenol, for example 1.1 to 2 times, and preferably 1.2 to 1.5 times the equivalent weight of the hydroxyl groups. The reaction is preferably accelerated with use of a solvent which forms an azeotrope with water, such as benzene, toluene, xylene, chlorobenzene or anisole.

Thereafter, the alkali metal salt of bisphenol is reacted with a benzonitrile compound substituted with a halogen atom such as chlorine and with a nitrile group.

Examples of the benzonitrile groups include 2,6-dichlorobenzonitrile, 2,6-difluorobenzonitrile, 2,5-dichlorobenzonitrile, 2,5-difluorobenzonitrile, 2,4-dichlorobenzonitrile, 2,4-difluorobenzonitrile, 2,6-dinitrobenzonitrile, 2,5-dinitrobenzonitrile and 2,4-dinitrobenzonitrile. Of these, the dichlorobenzonitrile compounds are preferable, and 2,6-dichlorobenzonitrile is more preferable.

The benzonitrile compound may be used in an amount 1.0001 to 3 times, and preferably 1.001 to 2 times the moles of the bisphenol. The reaction may be followed by further reaction by adding in excess, for example, 2,6-dichlorobenzonitrile to make the molecule terminated with a chlorine atom at both ends. When the difluorobenzonitrile or dinitrobenzonitrile compound is used, the reaction must be designed so as to afford a molecule terminated with a chlorine atom at both ends, for example by adding a dichlorobenzonitrile compound in the second half of the reaction.

The reaction temperature is in the range of 60 to 300° C., and preferably 80 to 250° C. The reaction time ranges from 15 minutes to 100 hours, and preferably from 1 to 24 hours.

The oligomer or polymer obtained may be purified by the conventional method, for example by dissolution and precipitation. Control of the molecular weight is made by altering the molar ratio of the excess aromatic dichloride and bisphenol used in the reaction. Since the nitrile-substituted aromatic dichloride has been used in excess, the resulting oligomer or polymer has a molecule terminated with a nitrile-substituted aromatic chloride.

The following are specific examples of the oligomers or polymers terminated with nitrile-substituted aromatic chlorides:

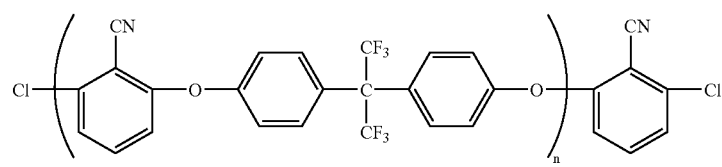

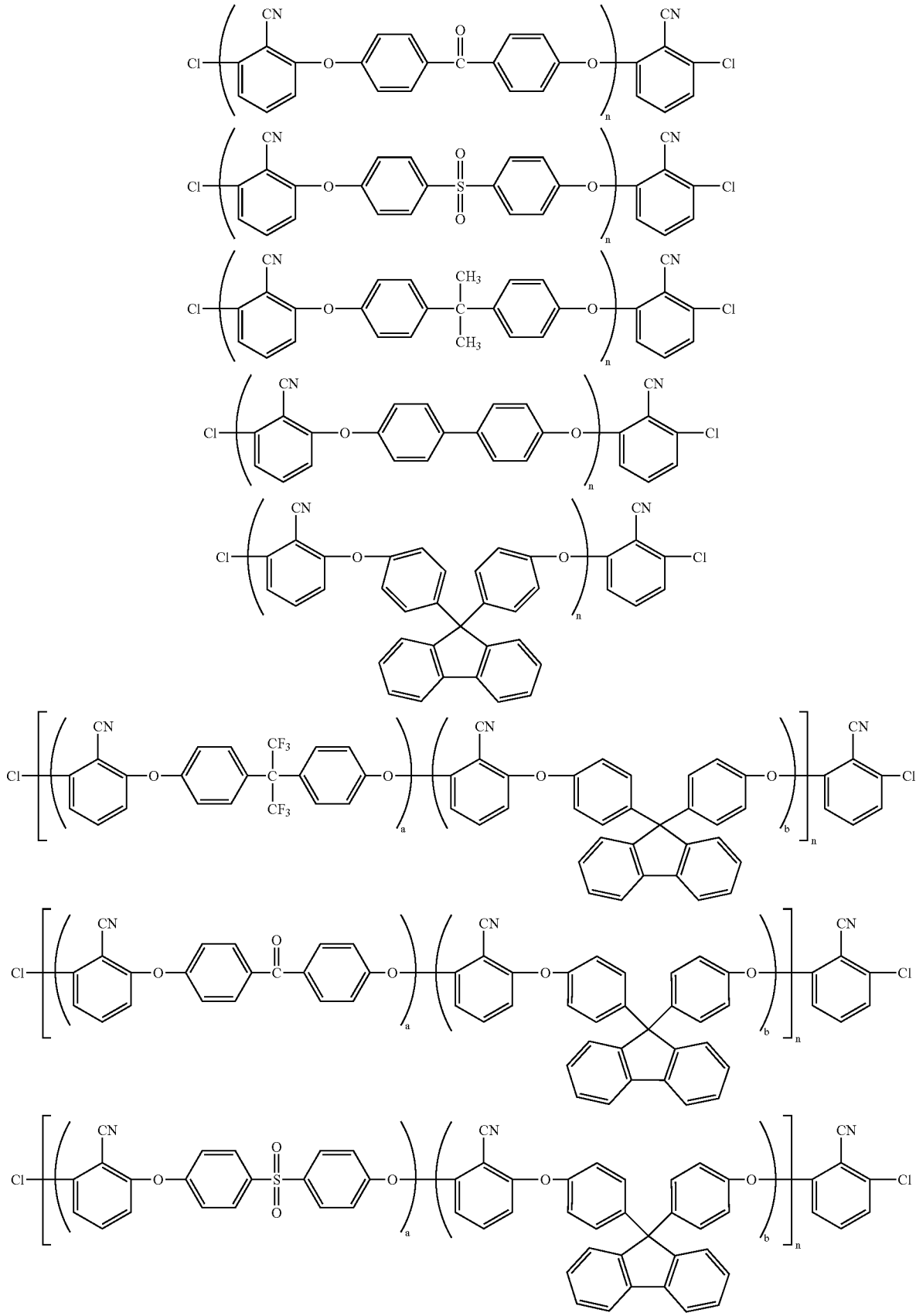

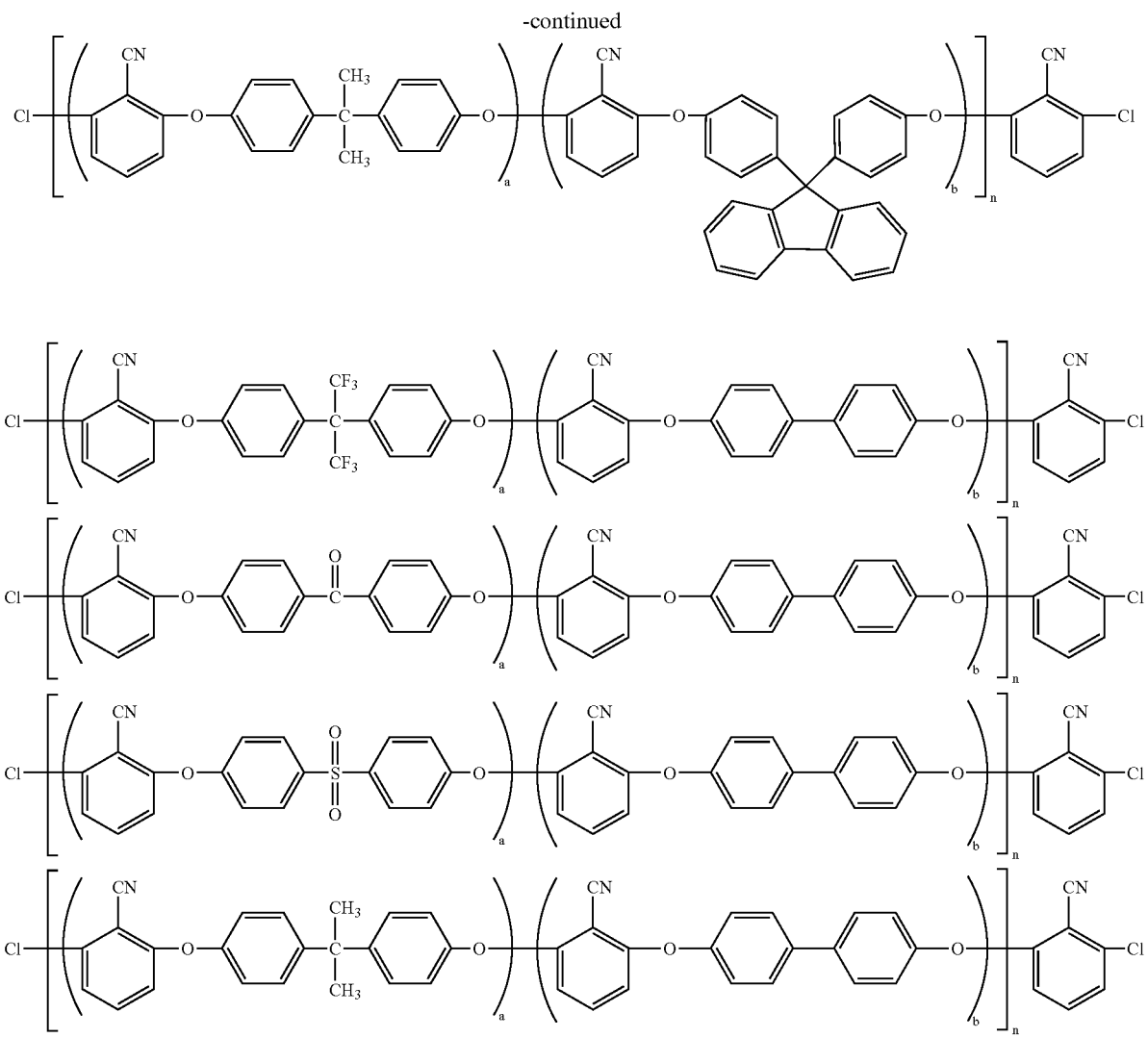

(Polyarylene Polymer)

The polyarylene polymer of the present invention may be a homopolymer consisting essentially of repeating units represented by the following formula (1') (hereinafter repeating units (1')), or may be a copolymer comprising the repeating units (1') and other repeating units. In either case, the polymer ranges in GPC weight-average molecular weight in terms of polystyrene (hereinafter weight-average molecular weight) from 10000 to 1,000,000, and preferably from 20000 to 800,000.

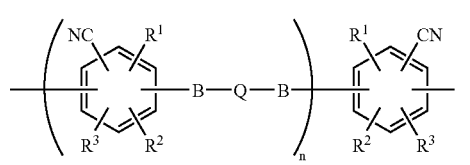

In the formula (1'), $R^1$ to $R^3$, B, Q and n are the same as in the formula (1).

The repeating units other than the repeating units (1') that constitute the polyarylene polymer are preferably represented by the formula (2) given below (hereinafter repeating units (2)):

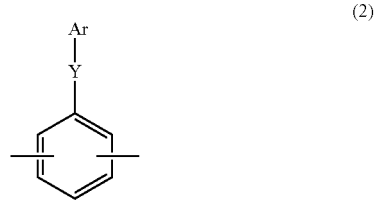

wherein Y is a divalent atom or organic group, or a direct bond. Examples thereof include electron-attracting groups such as —CO—, —CONH—, —(CF$_2$)$_p$— (where p is an integer of 1 to 10), —C(CF$_3$)$_2$—, —COO—, —SO— and —SO$_2$—, and electron-donating groups such as —O—, —S—, —CH=CH—, —C≡C— and groups represented by:

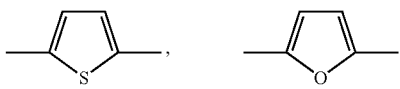

As Y the electron-attracting groups, particularly —CO— and —SO$_2$—, are preferable since their use leads to the sulfonated polyarylene polymers having enhanced acid strength and higher temperatures for elimination of the sulfonic groups.

Ar denotes an aromatic group, and examples thereof include phenyl, naphthyl, pyridyl, phenoxyphenyl, phenylphenyl and naphthoxyphenyl groups. The aromatic groups may have substituent groups.

The monomer that gives the structure of the repeating units (2) is represented by the following formula (2m):

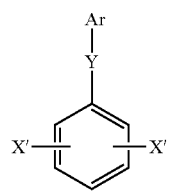

(2m)

wherein X' is an atom or a group selected from halogen atoms other than fluorine (i.e., chlorine, bromine and iodine), —OSO$_2$CH$_3$ and —OSO$_2$CF$_3$, and Y and Ar are the same as in the formula (2).

For the application of the polyarylene polymer containing the repeating units (1') and (2) as proton conductive membrane materials, the repeating units (2) preferably have a sulfonic group or a sulfonate group. To obtain such sulfonated polyarylene polymer, it is appropriate to sulfonate the polyarylene polymer with a sulfonating agent or to copolymerize using the monomer of the formula (2m) that has been sulfonated.

The sulfonated monomers of the formula (2m) include compounds listed below:

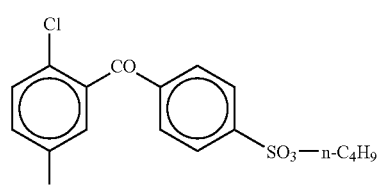

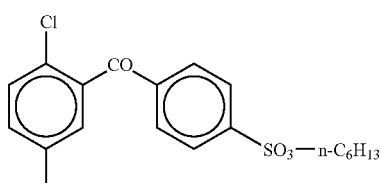

-continued

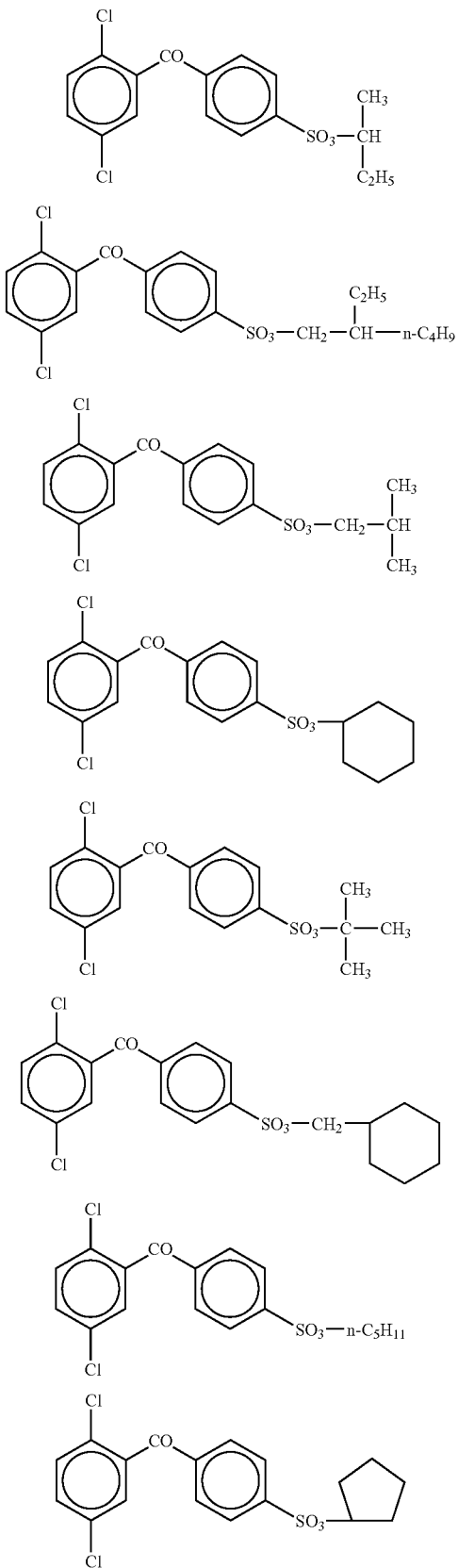

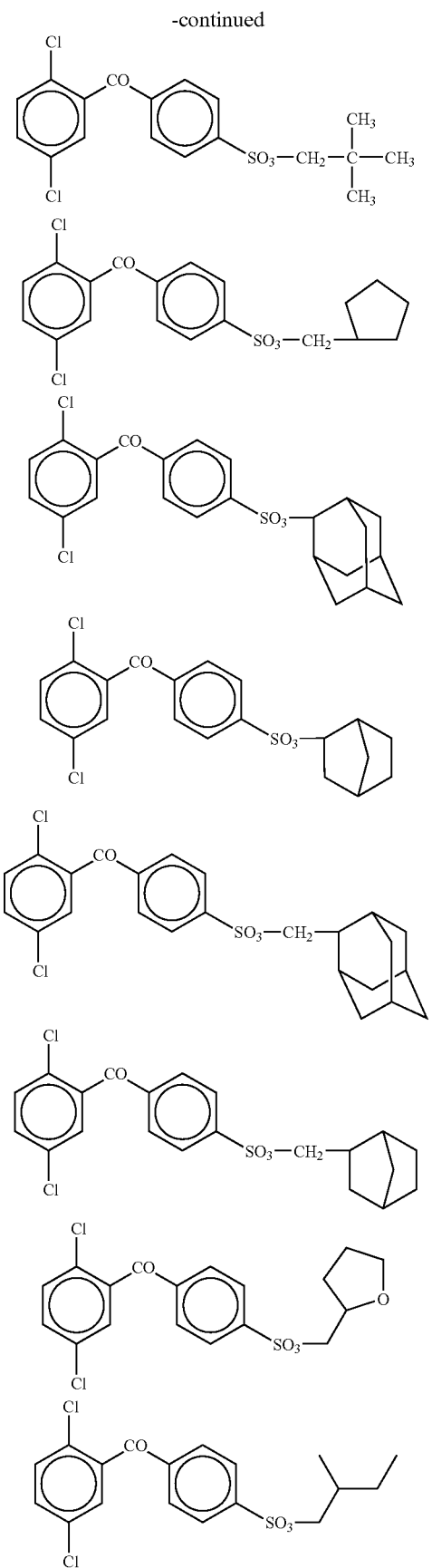

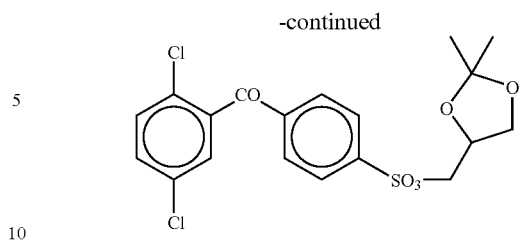

Also employable are corresponding to the above compounds except that the chlorine atom is replaced by a bromine atom, the —CO— group is replaced by the —SO$_2$— group, or these two replacements occur at the same time.

The ester groups in the above compounds are preferably derived from a primary alcohol, and the β carbon atoms are preferably tertiary or quaternary. More preferably, the ester groups are derived from a primary alcohol and the β carbon atoms are quaternary. When these two conditions are satisfied, excellent stability may be obtained during polymerization and no inhibited polymerization or crosslinking will result from the formation of sulfonic acids by deesterification.

The aromatic sulfonate derivatives as described above may be synthesized by the following methods:

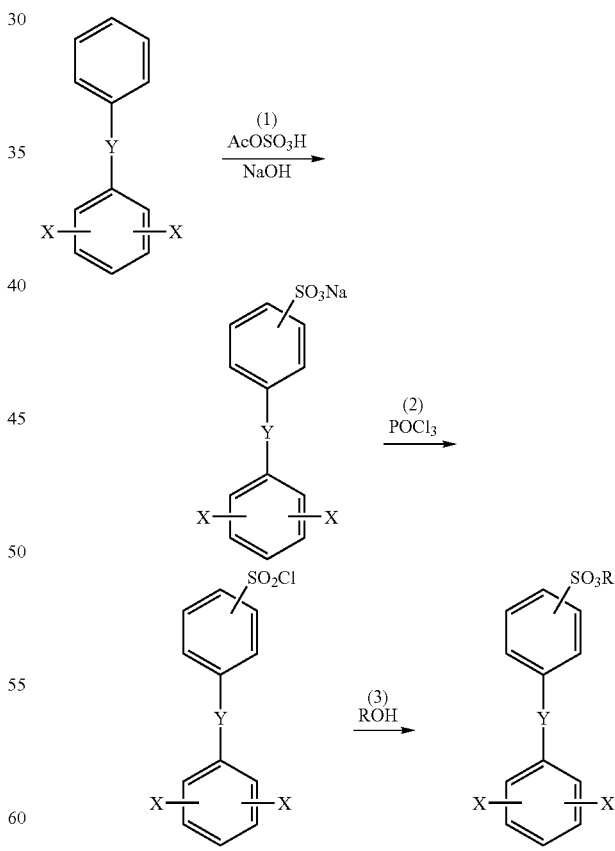

(1) Sulfonation (Introduction of Sodium Sulfonate Group)

For example, a 1,2-dichloromethane solution of 2,5-dichlorobenzophenone is reacted with a 1,2-dichloromethane solution containing acetyl sulfate in a molar amount five times that of 2,5-dichlorobenzophenone, at 60° C. for 3 to 5 hours. The reaction is terminated by addition of 1-propanol, and the reaction liquid is poured into an aqueous solution containing NaOH in a molar amount three times that of 2,5-dichlorobenzophenone. The resulting solution is concentrated to give sodium sulfonate fine powder.

(2) Conversion to Sulfonic Acid Chloride Group

For example, sodium 2,5-dichlorobenzophenone-3'-sulfonate is dissolved in about three to four times its weight of a mixed solvent consisting of sulfolane and acetonitrile in 4/6 volume ratio. The resultant solution is heated to 70° C., and phosphoryl chloride is added thereto to carry out reaction around 10° C. for about 5 hours. After the reaction, the reaction liquid is diluted with a large excess of cold water to precipitate the product, followed by filtration. The product is thereafter subjected to recrystallization with toluene to afford a purified crystal.

The sulfonic acid chloride occurs directly without this process if the acetyl sulfate used in (1) is replaced with 5 to 10-fold molar amount of chlorosulfonic acid.

(3) Conversion to Sulfonate Group 2,5-Dichlorobenzophenone-3'-sulfonic acid chloride is added dropwise to a cold mixed solution consisting of at least equimolar amounts (generally 1 to 3 times the moles of the sulfonic acid chloride) of i-butyl alcohol and pyridine, to carry out reaction. The reaction is temperature controlled up to 20° C. The reaction time depends on the reaction scale but is generally about 10 minutes to 5 hours. The reaction mixture is then treated with dilute hydrochloric acid and washed with water, and thereafter the objective product is extracted with ethyl acetate. After the extract is concentrated, the objective product is separated and recrystallized with methanol.

In the polyarylene polymer having the repeating units (1') and (2), the repeating units (1') account for 0.001 to 90 mol %, and preferably 0.1 to 80 mol %. When the content of the repeating units (1') exceeds 90 mol %, sulfonation of the copolymer results in an insufficient amount of sulfonic groups introduced, possibly leading to poor proton conductivity.

(Synthesis of Polyarylene Polymer)

The polyarylene polymer of the invention may be obtained by reacting the compound of the formula (1) (monomer (1)) with the compound of the formula (2m) (monomer (2)) in the presence of a catalyst that contains a transition metal compound. The monomer (1) is used at 0.001 to 90 mol %, and preferably 0.1 to 80 mol %, and the monomer (2) at 99.999 to 10 mol %, and preferably 99.9 to 20 mol % based on all the monomers combined.

The catalyst used in the copolymerization is a catalyst system containing a transition metal compound. This catalyst system essentially contains (1) a transition metal salt and a compound which functions as a ligand (hereinafter "ligand component"), or a transition metal complex (including a copper salt) to which a ligand is coordinated, and (2) a reducing agent. A "salt" may be added to increase the polymerization rate.

Examples of the transition metal salt include nickel compounds such as nickel chloride, nickel bromide, nickel iodide and nickel acetylacetonate; palladium compounds such as palladium chloride, palladium bromide and palladium iodide; iron compounds such as iron chloride, iron bromide and iron iodide; and cobalt compounds such as cobalt chloride, cobalt bromide and cobalt iodide. Of these, nickel chloride, nickel bromide, etc. are particularly preferred.

Examples of the ligand component include triphenylphosphine, 2,2'-bipyridine, 1,5-cyclooctadiene and 1,3-bis(diphenylphosphino)propane. Of these, triphenylphosphine and 2,2'-bipyridine are preferred. The ligand components may be used singly or in combination of two or more kinds.

Examples of the transition metal complex with a coordinated ligand include
nickel chloride-bis(triphenylphosphine),
nickel bromide-bis(triphenylphosphine),
nickel iodide-bis(triphenylphosphine),
nickel nitrate-bis-(triphenylphosphine),
nickel chloride(2,2'-bipyridine),
nickel bromide(2,2'-bipyridine),
nickel iodide(2,2'-bipyridine),
nickel nitrate(2,2'-bipyridine),
bis(1,5-cyclooctadiene)nickel,
tetrakis(triphenylphosphine)nickel,
tetrakis(triphenylphosphite)nickel and
tetrakis(triphenylphosphine)palladium. Of these, nickel chloride-bis(triphenylphosphine) and nickel chloride(2,2'-bipyridine) are preferred.

Examples of the reducing agent employable in the aforesaid catalyst system include iron, zinc, manganese, aluminum, magnesium, sodium, calcium and the like. Of these, zinc, magnesium and manganese are preferable. These reducing agents may be used in a more activated form by contact with an acid, for example, an organic acid.

Examples of the "salt" employable in the catalyst system include sodium compounds such as sodium fluoride, sodium chloride, sodium bromide, sodium iodide and sodium sulfate; potassium compounds such as potassium fluoride, potassium chloride, potassium bromide, potassium iodide and potassium sulfate; and ammonium compounds such as tetraethylammonium fluoride, tetraethylammonium chloride, tetraethylammonium bromide, tetraethylammonium iodide and tetraethylammonium sulfate. Of these, sodium bromide, sodium iodide, potassium bromide, tetraethylammonium bromide and tetraethylammonium iodide are preferred.

In respect of the proportion of the above components, the transition metal salt or the transition metal complex is generally used in an amount of 0.0001 to 10 mol, and preferably 0.01 to 0.5 mol, per mol of the monomers combined. If the amount is less than 0.0001 mol, the polymerization may not proceed to a desired level. Contrary, the amount exceeding 10 mol may result in a lower molecular weight of the polymer.

When the catalyst system contains the transition metal salt and the ligand component, the ligand component is generally used in an amount of 0.1 to 100 mol, and preferably 1 to 10 mol, per mol of the transition metal salt. If the amount is less than 0.1 mol, the catalytic activity may become insufficient. Contrary, the amount exceeding 100 mol may result in a lower molecular weight of the polymer.

The amount of the reducing agent is usually in the range of 0.1 to 100 mol, and preferably 1 to 10 mol, per mol of the monomers combined. If the reducing agent has an amount less than 0.1 mol, the polymerization may not proceed sufficiently. Contrary, the amount thereof exceeding 100 mol may lead to difficult purification of the resulting polymer.

When the "salt" is used, the amount thereof is usually 0.001 to 100 mol, and preferably 0.01 to 1 mol, per mol of the monomers combined. If the salt has an amount less than 0.001 mol, it often cannot achieve sufficient effect of increasing the polymerization rate. Contrary, the amount thereof exceeding 100 mol may lead to difficult purification of the resulting polymer.

Exemplary polymerization solvents include tetrahydrofuran, cyclohexanone, dimethyl sulfoxide, N,N-dimethylformamide, N,N-dimethylacetamide, N-methyl-2-pyrrolidone, γ-butyrolactone, sulfolane, γ-butyrolactam, dimethylimidazolidinone and tetramethylurea. Of these, tetrahydrofuran, N,N-dimethylformamide, N,N-dimethylacetamide and N-methyl-2-pyrrolidone are preferred. These polymerization solvents are desirably used after dried sufficiently.

The concentration of the monomers in the polymerization solvent is usually in the range of 1 to 90 wt %, and preferably 5 to 40 wt %. The polymerization temperature is usually 0 to 200° C., and preferably 50 to 120° C. The polymerization time is usually 0.5 to 100 hours, and preferably 1 to 40 hours.

The polyarylene polymer obtained as described above has a weight-average molecular weight of 10,000 to 1,000,000, and preferably 20,000 to 800,000 in terms of polystyrene according to gel permeation chromatography (GPC). When the weight-average molecular weight is less than 10,000, insufficient film properties are encountered such as cracked films, and strength characteristics are also unsatisfactory. On the other hand, when the weight-average molecular weight exceeds 1,000,000, the polymer will have insufficient solubility, and its solution has a high viscosity to cause bad processability.

(Polyarylene Polymer with Sulfonic Groups)

The polyarylene polymer with sulfonic groups may be obtained by treating the above polymer having no sulfonic groups with a sulfonating agent according to a common method thereby to introduce sulfonic groups in the polymer. The sulfonation may be achieved by treating the copolymer with a conventional sulfonating agent under known conditions. Exemplary sulfonating agents include sulfuric anhydride, fuming sulfuric acid, chlorosulfonic acid, sulfuric acid and sodium hydrogensulfite. (See Polymer Preprints, Japan, vol. 42, No. 3, p. 730 (1993), Polymer Preprints, Japan, vol. 43, No. 3, p. 736 (1994), and Polymer Preprints, Japan, vol. 42, No. 7, pp. 2490–2492 (1993)).

Specifically, the sulfonation may be carried out by reacting the copolymer having no sulfonic groups with the sulfonating agent in the presence or absence of a solvent. The solvents used herein include hydrocarbon solvents such as n-hexane; ether solvents such as tetrahydrofuran and dioxane; aprotic polar solvents such as dimethylacetamide, dimethylformamide and dimethyl sulfoxide; and halogenated hydrocarbons such as tetrachloroethane, dichloroethane, chloroform and methylene chloride. The reaction temperature is not particularly limited, but is usually in the range of −50 to 200° C., and preferably −10 to 100° C. The reaction time is usually 0.5 to 1,000 hours, and preferably 1 to 200 hours.

When the monomer giving the structure of the repeating units (2) has a sulfonate group and consequently the polyarylene polymer synthesized possesses sulfonate groups, the polymer may be hydrolyzed to convert the sulfonate groups (—SO$_3$R) of the repeating units (2) to the sulfonic groups (—SO$_3$H), thereby obtaining the polyarylene polymer with sulfonic groups.

For example, the hydrolysis may be performed by any of the following methods:

(1) The polyarylene polymer with sulfonate groups is added to an excess of water or an alcohol that contains a small amount of hydrochloric acid, and the mixture is stirred for at least 5 minutes.

(2) The polyarylene polymer with sulfonate groups is reacted in trifluoroacetic acid at about 80 to 120° C. for about 5 to 10 hours.

(3) The polyarylene polymer with sulfonate groups is reacted in a solution such as N-methylpyrrolidone that contains lithium bromide in a molar amount 1 to 3 times that of the sulfonate groups (—SO$_3$R) of the polymer, at about 80 to 150° C. for about 3 to 10 hours, and thereafter hydrochloric acid is added to the reaction product.

In the invention, it is preferable that at least 90% of the sulfonate groups (—SO$_3$R) of the polyarylene polymer are converted to the sulfonic groups (—SO$_3$H).

The sulfonated polyarylene polymer obtained as described above contains the sulfonic groups in an amount of 0.5 to 3 meq/g, and preferably 0.8 to 2.8 meq/g. If the sulfonic groups have a proportion below 0.5 meq/g, the proton conductivity will become poor. On the other hand, the amount thereof over 3 meq/g will cause the polymer to have so high a hydrophilicity that it becomes less durable or, even worse, soluble in water or hot water.

The sulfonic group content may be readily controlled by altering the proportion between the monomers (1) and (2m), or by changing the type or combination of the monomers.

The structure of the sulfonated polyarylene polymer may be determined from its infrared absorption spectrum, for example the S=O absorption at 1030 to 1045 cm$^{-1}$ and at 1160 to 1190 cm$^{-1}$, the C—O—C absorption at 1130 to 1250 cm$^{-1}$ and the C=O absorption at 1640 to 1660 cm$^{-1}$. The composition ratio of these may be obtained by neutralization titration of the sulfonic acid or elemental analysis. The structure may be determined also from the peaks of aromatic protons at 6.8–8.0 ppm in the nuclear magnetic resonance spectrum ($^1$H-NMR).

(Solid Polymer Electrolyte)

The solid polymer electrolyte according to the invention comprises the above-described sulfonated polyarylene polymer. It may further contain an antioxidant such as a phenolic hydroxyl group-containing compound, an amine compound, an organophosphorus compound or an organosulfur compound, without adversary affecting the proton conductivity.

The solid polymer electrolyte may be used in any forms including particles, fibers and membranes, as required depending on the applications. For example, membranes (so-called proton conductive membranes) are desirable in electrochemical device applications such as fuel cells and water hydrolysis devices.

(Proton Conductive Membrane)

The proton conductive membrane of the invention is made from the solid polymer electrolyte comprising the sulfonated polyarylene polymer. Production of the proton conductive membrane may employ, together with the solid polymer electrolyte, inorganic acids such as sulfuric acid and phosphoric acid, organic acids including carboxylic acids, an appropriate amount of water, and the like.

For example, the proton conductive membrane may be produced by a casting method in which the sulfonated polyarylene polymer dissolved in a solvent is flow-cast over a substrate to form a film. The substrate used herein is not particularly limited and may be selected from those substrates commonly used in the solution casting methods. Examples thereof include plastic substrates and metal substrates. Preferably, thermoplastic resin substrates such as polyethyleneterephthalate (PET) films are used.

The solvents to dissolve the sulfonated polyarylene polymer include aprotic polar solvents such as N-methyl-2-pyrrolidone, N,N-dimethylformamide, γ-butyrolactone, N,N-dimethylacetamide, dimethylsulfoxide, dimethylurea and dimethylimidazolidinone. In view of solvent properties and solution viscosity, N-methyl-2-pyrrolidone (hereinafter "NMP") is preferable. The aprotic polar solvents may be used singly or in combination of two or more kinds.

The solvent for dissolving the sulfonated polyarylene polymer may be a mixed solvent of the above aprotic polar solvent and an alcohol. Exemplary alcohols include methanol, ethanol, propyl alcohol, isopropyl alcohol, sec-butyl alcohol and tert-butyl alcohol. In particular, methanol is preferable since it ensures an appropriately low solution viscosity over a wide range of proportions of the polymer. These alcohols may be used singly or in combination of two or more kinds.

The above mixed solvent will contain the aprotic polar solvent in an amount of 95 to 25 wt %, and preferably 90 to 25 wt %, and the alcohol in an amount of 5 to 75 wt %, and preferably 10 to 75 wt % (the total of these two is 100 wt %). This proportion of the alcohol leads to an appropriately low solution viscosity.

Although the concentration of the sulfonated polyarylene polymer in the solution (i.e. the polymer concentration) depends on the molecular weight of the sulfonated polyarylene polymer, it is generally from 5 to 40 wt %, and preferably from 7 to 25 wt %. The polymer concentration less than 5 wt % causes difficulties in producing the membrane in large thickness and results in easy occurrence of pinholes. On the other hand, when the polymer concentration goes over 40 wt %, the solution viscosity becomes so high that the film production will be difficult and further that the obtained film may have low surface smoothness.

The solution viscosity may vary depending on the molecular weight of the sulfonated polyarylene polymer or the polymer concentration. Generally, it ranges from 2,000 to 100,000 mPa·s, and preferably from 3,000 to 50,000 mPa·s. When the viscosity is less than 2,000 mPa·s, the solution will have too high a fluidity and may spill out of the substrate during the membrane production. On the contrary, the viscosity over 100,000 mPa·s is so high that the solution cannot be extruded through a die and the flow-casting for the film production may be difficult.

The wet film obtained as described above may be soaked into water to substitute the remaining organic solvent in the film with water. This treatment enables reduction of the amount of the residual solvent in the proton conductive membrane.

Prior to the soak into water, the wet film may be predried. The predrying may be performed by maintaining the wet film at 50 to 150° C. for 0.1 to 10 hours.

Soaking the wet films in water may be carried out batchwise with respect to each sheet, or may be a continuous process where the films, which may be in the original form of laminate with a substrate film (e.g. PET film) as produced or which may be released from the substrate, are soaked in water and then wound sequentially.

In the batchwise soaking, the films are suitably framed or fixed by similar means to prevent wrinkles from forming on the surface of treated films.

The soaking should be suitably made so that the wet films would contact with water that is at least 10 parts by weight, and preferably at least 30 parts by weight based on 1 part by weight of the wet films. This contact ratio is suitably as large as possible to minimize the amount of solvent remaining in the proton conductive membrane. In order to reduce the residual solvent amount in the proton conductive membrane, it is also effective to keep the concentration of the organic solvent in water at or below a certain level by renewing the water used in the soaking or by letting the water overflow. The in-plane distribution of the organic solvent within the proton conductive membrane may be effectively uniformed by homogenizing the organic solvent concentration in the water by stirring or the like.

When the wet film is soaked in water, the water preferably has a temperature of 5 to 80° C. Although the substitution between the organic solvent and water can take place at a higher rate as the water temperature rises, the water absorption of the film will also increase at higher temperatures. Accordingly, there is a concern that the proton conductive membrane has a rough surface after dried. In general, the water temperature is suitably 10 to 60° C. from the viewpoints of the substitution rate and easy handling.

The soaking time varies depending on the initial amount of residual solvent, the water-solvent contact ratio and the water temperature. Generally, the soaking time ranges from 10 minutes to 240 hours, and preferably from 30 minutes to 100 hours.

When the water-soaked film is dried, a proton conductive membrane is obtained that has a reduced amount of residual solvent, generally 5 wt % or below.

Controlling the soaking conditions enables reduction of the residual solvent down to 1 wt % or less of the proton conductive membrane. For example, this is possible when the wet film is soaked in water that is at least 50 parts by weight based on 1 part by weight of the wet film at a water temperature of 10 to 60° C. for 10 minutes to 10 hours.

After the wet film has been soaked in water as described above, the film is dried at 30 to 100° C., preferably 50 to 80° C., for 10 to 180 minutes, preferably 15 to 60 minutes. Subsequently, it is vacuum dried at 50 to 150° C. and preferably at 500 to 0.1 mmHg for 0.5 to 24 hours. The proton conductive membrane according to the invention may be thus obtained.

The proton conductive membrane will range in dry thickness from 10 to 100 μm, and preferably from 20 to 80 μm.

When the polyarylene polymer with sulfonate groups is formed into a film by the above method without undergoing hydrolysis, this film may be hydrolyzed by the above method to yield a proton conductive membrane comprising the sulfonated polyarylene polymer.

The proton conductive membrane may contain an anti-aging agent, preferably a hindered phenol compound with a molecular weight of not less than 500. Such anti-aging agents provide longer durability of the proton conductive membrane.

The hindered phenol compounds employable in the invention whose molecular weight is 500 or more include triethyleneglycol-bis[3-(3-t-butyl-5-methyl-4-hydroxyphenyl)propionate] (trade name: IRGANOX 245), 1,6-hexanediol-bis[3-(3,5-di-t-butyl-4-hydroxyphenyl)propionate] (trade name: IRGANOX 259), 2,4-bis-(n-octylthio)-6-(4-hydroxy-3,5-di-t-butylanilino)-3,5-triadine (trade name: IRGANOX 565), pentaerythrithyl-tetrakis[3-(3,5-di-t-butyl-4-hydroxyphenyl)propionate] (trade name: IRGANOX 1010), 2,2-thio-diethylene bis[3-(3,5-di-t-butyl-4-hydroxyphenyl)propionate] (trade name: IRGANOX 1035), octadecyl-3-(3,5-di-t-butyl-4-hydroxyphenyl)propionate] (trade name: IRGANOX 1076), N,N-hexamethylenebis (3,5-di-t-butyl-4-hydroxy-hydrocinnamide) (trade name: IRGANOX 1098), 1,3,5-trimethyl-2,4,6-tris(3,5-di-t-butyl-4-hydroxybenzyl)

benzene (trade name: IRGANOX 1330), tris-(3,5-di-t-butyl-4-hydroxybenzyl)-isocyanurate (trade name: IRGANOX 3114) and 3,9-bis[2-[3-(3-t-butyl-4-hydroxy-5-methylphenyl)propionyloxy]-1,1-dimethylethyl]-2,4,8,10-tetraoxaspiro[5.5]undecane (trade name: Sumilizer GA-80).

The hindered phenol compound with 500 or more molecular weight will preferably be used in an amount of 0.01 to 10 parts by weight based on 100 parts by weight of the sulfonated polyarylene polymer.

The proton conductive membrane of the invention can be suitably used as electrolytes for primary and secondary batteries, solid polymer electrolytes for fuel cells and other proton conductive membranes for display elements, sensors, signaling media, solid condensers and ion exchange membranes.

EXAMPLES

The present invention will be hereinafter described in greater detail by Examples presented below, but it should be construed that the invention is in no way limited to those Examples. In Examples, the following properties were measured as described below.

(Molecular Weight)

Before sulfonation, the hydrophobic units were analyzed by GPC in a tetrahydrofuran (THF) solvent to determine the number-average molecular weight (Mn) in terms of polystyrene. The sulfonated polymer's weight-average molecular weight (Mw) in terms of polystyrene was measured by GPC using, as an eluting solution, N-methyl-2-pyrrolidone (NMP) containing lithium bromide and phosphoric acid.

(Ion Exchange Capacity)

The sulfonated polymer was washed until the pH of the washings reached 4 to 6, and free residual acids were removed. The polymer was then sufficiently washed with water and dried. A predetermined amount of the polymer was weighed out and dissolved in a THF/water mixed solvent. The solution mixed with phenolphthalein as an indicator was titrated with an NaOH standard solution to obtain a point of neutralization, from which the ion exchange capacity was determined.

(Proton Conductivity)

A 5 mm-wide strip specimen of the proton conductive membrane, holding 5 platinum wires (0.5 mm diameter) at intervals of 5 mm on its surface, was placed in a thermo-hygrostat. Subsequently, the alternating current impedance between the platinum wires was measured at 85° C., 90% RH and 10 kHz. This measurement was carried out using a chemical impedance measuring system (NF Corporation) and thermo-hygrostat JW241 (Yamato Science Co., Ltd.). The alternating current resistance was measured in each case where the interwire distance was changed from 5 mm to 20 mm among the 5 platinum wires. The resistivity of the membrane was calculated by the following equation from a gradient between the interwire distance and the resistance. The reciprocal number of resistivity was obtained as the alternating current impedance, from which the proton conductivity was calculated.

Resistivity $R$ ($\Omega \cdot cm$)=0.5 (cm)×membrane thickness (cm)×resistance/interwire distance gradient ($\Omega$/cm)

(Thermal Decomposition Temperature)

The sulfonated polymer was analyzed by TGA (nitrogen atmosphere, 20° C./min heating rate) to obtain a decomposition temperature as the thermal decomposition (initiation) temperature.

(Hot Water Resistance)

The sulfonated polymer film having 50 μm thickness was soaked in 120° C. hot water in a pressure cooker for 24 hours. The weight difference of the soaked film from the original weight was obtained to measure the weight retention.

(Fenton's Reagent Resistance)

To prepare a Fenton's reagent, iron sulfate heptahydrate was added to a 3-wt % hydrogen peroxide aqueous solution to achieve 20 ppm iron ion concentration. Of the Fenton's reagent thus prepared, a 200 g portion was introduced into a 250 cc polyethylene container. Subsequently, the sulfonated polymer film having 55 μm thickness and cut into a size of 3×4 cm was placed in the container. The container was then closed and immersed for 10 hours in a liquid bath temperature controlled at 45° C. Thereafter, the film was taken out, washed with ion exchange water, and dried at 25° C. and 50% RH for 12 hours. The weight change of the treated film from the original weight was obtained to measure the weight retention.

Example 1

Synthesis of Hydrophobic Units

A 1-L three-necked flask equipped with a stirrer, a thermometer, a Dean-stark tube, a nitrogen inlet tube and a cooling tube, was charged with 48.8 g (284 mmol) of 2,6-dichlorobenzonitrile, 89.5 g (266 mmol) of 2,2-bis(4-hydroxyphenyl)-1,1,1,3,3,3-hexafluoropropane, and 47.8 g (346 mmol) of potassium carbonate. After the flask had been purged with nitrogen, 346 mL of sulfolane and 173 ml of toluene were added, followed by stirring. The reaction liquid was heated at 150° C. under reflux in an oil bath. Water resulting from the reaction was trapped in the Dean-stark tube. Water almost ceased to occur in 3 hours, and the toluene was removed outside the reaction system through the Dean-stark tube. Subsequently, the reaction temperature was slowly raised to 200° C. and stirring was performed for 3 hours. Thereafter, 9.2 g (53 mmol) of 2,6-dichlorobenzonitrile was added to carry out reaction for 5 hours.

After the reaction liquid had been cooled naturally, it was diluted with 100 mL of toluene. The reaction liquid was then filtered to remove insoluble inorganic salts, and the filtrate was poured into 2 L of methanol to precipitate the product. The precipitated product was filtered off, dried and dissolved in 250 mL of tetrahydrofuran. The thus-formed solution was poured into 2 L of methanol to perform reprecipitation. The precipitated white powder was filtered off and dried to yield 109 g of a desired product. GPC provided a number-average molecular weight (Mn) of 9500. $^1$H-NMR spectrum of the compound is shown in FIG. 1. This compound was confirmed to be an oligomer of the formula (I):

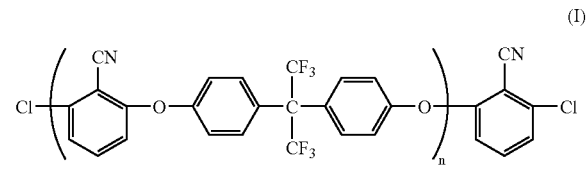

Example 2

Synthesis of Sulfonated Polymer

A 1-L three-necked flask equipped with a stirrer, a thermometer and a nitrogen inlet tube was charged with 135.2 g (337 mmol) of neopentyl 3-(2,5-dichlorobenzoyl)benzenesulfonate, 48.7 g (5.1 mmol) of the Mn-9500 hydrophobic units obtained in Example 1, 6.71 g (10.3 mmol) of bis(triphenylphosphine)nickel dichloride, 1.54 g (10.3 mmol) of sodium iodide, 35.9 g (137 mmol) of triphenylphosphine, and 53.7 g (821 mmol) of zinc. After the flask had been purged with dry nitrogen, 430 mL of N,N-dimethylacetamide (DMAc) was added and the mixture was stirred for 3 hours while maintaining the reaction temperature at 80° C. The reaction liquid was diluted with 730 mL of DMAc, and insolubles were filtered.

Figure 2:
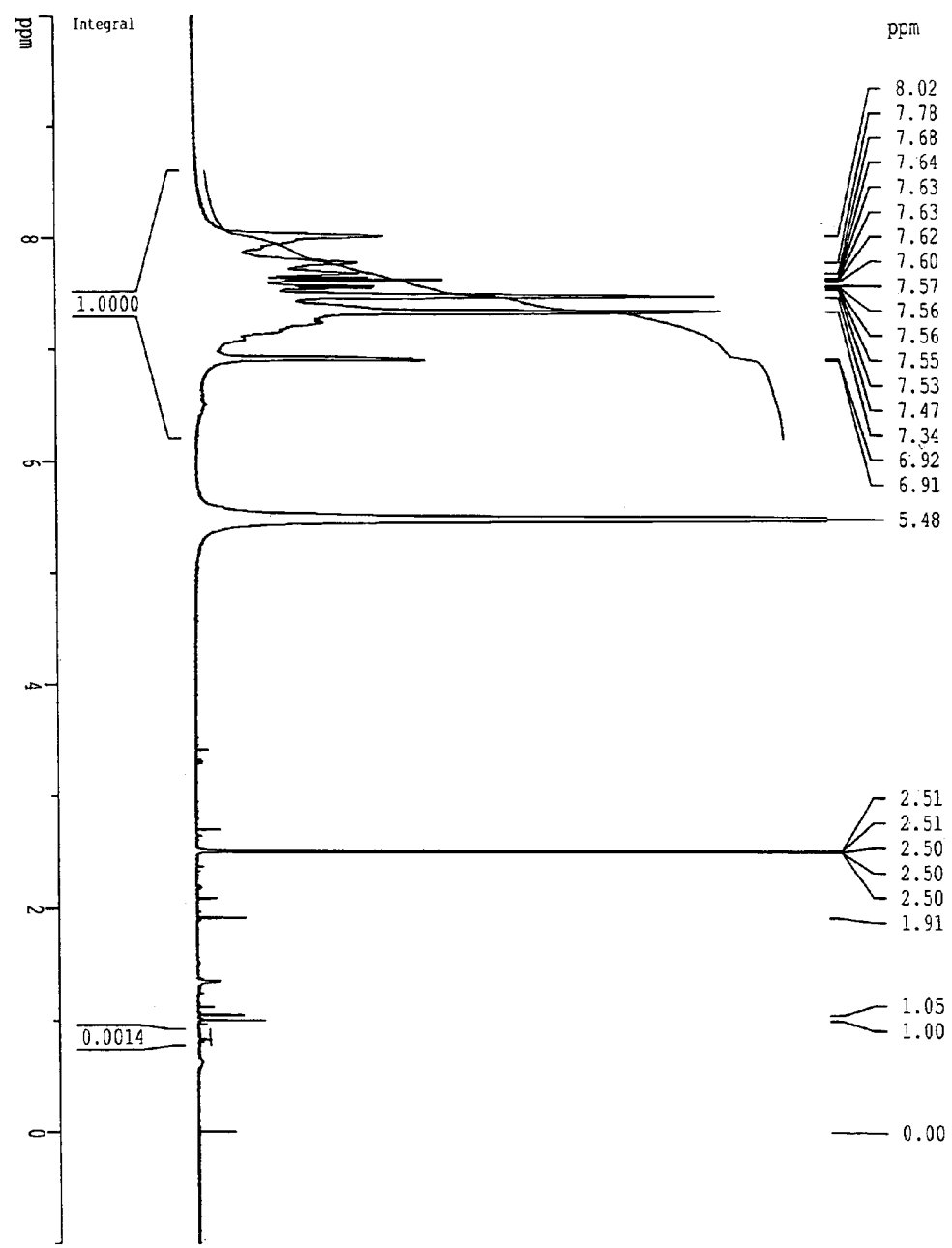
FIG. 2 is an NMR spectrum of the sulfonated polymer obtained in Example 2.

The solution obtained was then introduced into a 2-L three-necked flask equipped with a stirrer, a thermometer and a nitrogen inlet tube, and heated to 115° C. with stirring. Subsequently, 44 g (506 mmol) of lithium bromide was added. After the mixture had been stirred for 7 hours, it was poured into 5 L of aceton to precipitate the product. The product was then washed sequentially with 1N hydrochloric acid and with pure water, and dried to give 122 g of a desired polymer. The weight-average molecular weight (Mw) of the polymer was 135,000. $^1$H-NMR spectrum of the polymer is shown in FIG. 2. This polymer is assumed to be a sulfonated polymer represented by the formula (II):

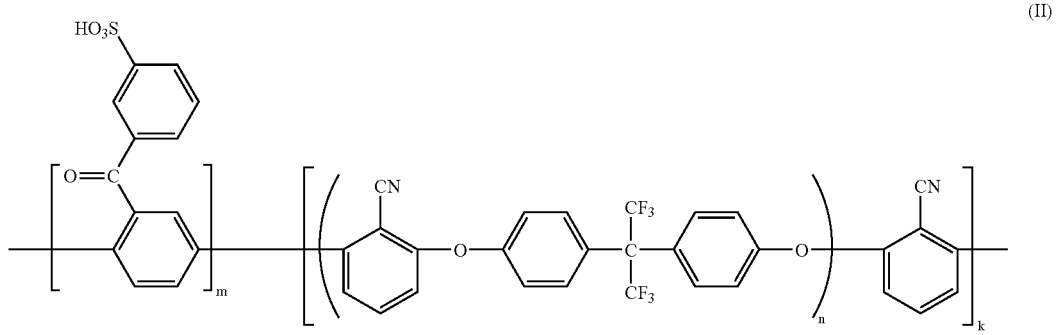

(II)

An 8 wt % solution of the sulfonated polymer in NMP was cast over a glass plate to form a coating. The coating was air dried and then vacuum dried to give a film having a dry thickness of 40 μm. The film was evaluated by the above methods. The results are shown in Table 1.

Example 3

Synthesis of Hydrophobic Units

Reaction was performed in the same manner as in Example 1, except that the flask was charged with 49.4 g (287 mmol) of 2,6-dichlorobenzonitrile, 88.4 g (263 mmol) of 2,2-bis(4-hydroxyphenyl)-1,1,1,3,3,3-hexafluoropropane and 47.3 g (342 mmol) of potassium carbonate. Thereafter, 12.3 g (72 mmol) of 2,6-dichlorobenzonitrile was added to carry out reaction for 5 hours. The reaction was followed by the same procedure as in Example 1, and 107 g of a desired product resulted. GPC provided a number-average molecular weight (Mn) of 7300.

Example 4

Synthesis of Sulfonated Polymer

A 1-L three-necked flask equipped with a stirrer, a thermometer and a nitrogen inlet tube was charged with 134.6 g (336 mmol) of neopentyl 3-(2,5-dichlorobenzoyl)benzenesulfonate, 47.4 g (6.5 mmol) of the Mn-7300 hydrophobic units obtained in Example 3, 6.71 g (10.3 mmol) of bis(triphenylphosphine)nickel dichloride, 1.54 g (10.3 mmol) of sodium iodide, 35.9 g (136 mmol) of triphenylphosphine, and 53.7 g (820 mmol) of zinc. Reaction was carried out by the procedure described in Example 2 to produce 129 g of a sulfonated polymer. The weight-average molecular weight (Mw) of the polymer was 140,000.

An 8 wt % solution of the sulfonated polymer in NMP was cast over a glass plate to form a coating. The coating was air dried and then vacuum dried to give a film having a dry thickness of 40 μm. The film was evaluated by the above methods. The results are shown in Table 1.

Example 5

Synthesis of Hydrophobic Units

A 1-L three-necked flask equipped with a stirrer, a thermometer, a Dean-stark tube, a nitrogen inlet tube and a cooling tube, was charged with 44.5 g (259 mmol) of 2,6-dichlorobenzonitrile, 102.0 g (291 mmol) of 9,9-bis(4-hydroxyphenyl)fluorene, and 52.3 g (379 mmol) of potassium carbonate. After the flask had been purged with nitrogen, 366 mL of sulfolane and 183 ml of toluene were added, followed by stirring. The reaction liquid was heated at 150° C. under reflux in an oil bath. Water resulting from the reaction was trapped in the Dean-stark tube. Water almost ceased to occur in 3 hours, and the toluene was removed outside the reaction system through the Dean-stark tube. Subsequently, the reaction temperature was slowly raised to 200° C. and stirring was performed for 3 hours. Thereafter, 16.7 g (97 mmol) of 2,6-dichlorobenzonitrile was added to carry out reaction for 5 hours.

Figure 3:
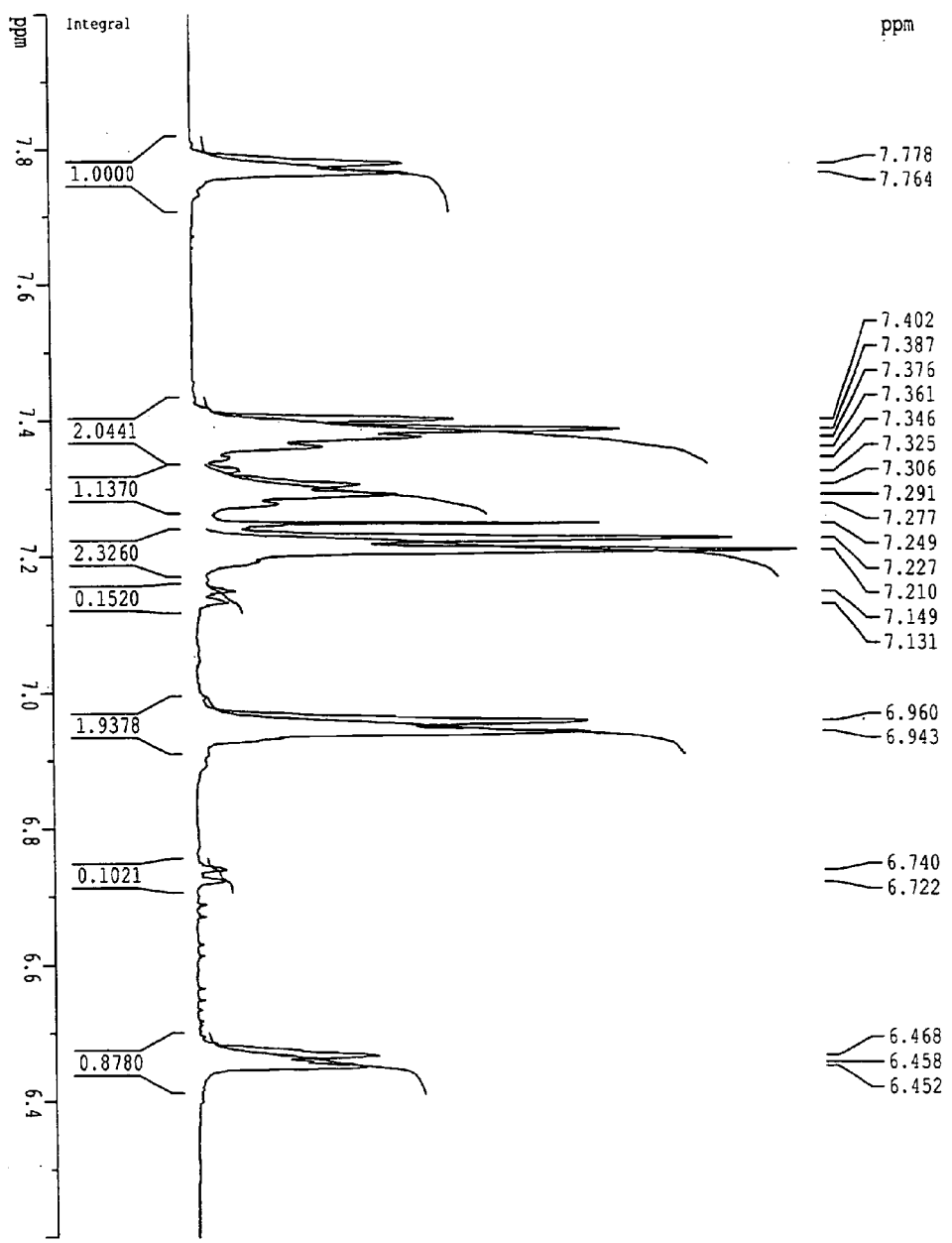
FIG. 3 is an NMR spectrum of the hydrophobic unit obtained in Example 5.

After the reaction liquid had been cooled naturally, it was diluted with 100 mL of toluene. The reaction liquid was then filtered to remove insoluble inorganic salts, and the filtrate was poured into 2 L of methanol to precipitate the product. The precipitated product was filtered off, dried and dissolved in 250 mL of tetrahydrofuran. The thus-formed solution was poured into 2 L of methanol to perform reprecipitation. The precipitated white powder was filtered off and dried to yield 118 g of a desired product. GPC provided a number-average molecular weight (Mn) of 7300. $^1$H-NMR spectrum of the compound is shown in FIG. 3. This compound was confirmed to be an oligomer of the formula (III):

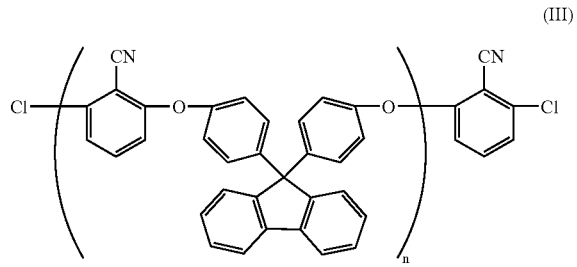

(III)

Example 6

Synthesis of Sulfonated Polymer

A 1-L three-necked flask equipped with a stirrer, a thermometer and a nitrogen inlet tube was charged with 207.5 g (517 mmol) of neopentyl 3-(2,5-dichlorobenzoyl) benzenesulfonate, 57.5 g (7.88 mmol) of the Mn-7300 hydrophobic units obtained in Example 5, 10.3 g (15.8 mmol) of bis(triphenylphosphine)nickel dichloride, 2.36 g (15.8 mmol) of sodium iodide, 55.1 g (210 mmol) of triphenylphosphine, and 82.4 g (1260mmol) of zinc. After the flask had been purged with dry nitrogen, 720 mL of N,N-dimethylacetamide (DMAc) was added and the mixture was stirred for 3 hours while maintaining the reaction temperature at 80° C. The reaction liquid was diluted with 1360 mL of DMAc, and insolubles were filtered.

Figure 4:
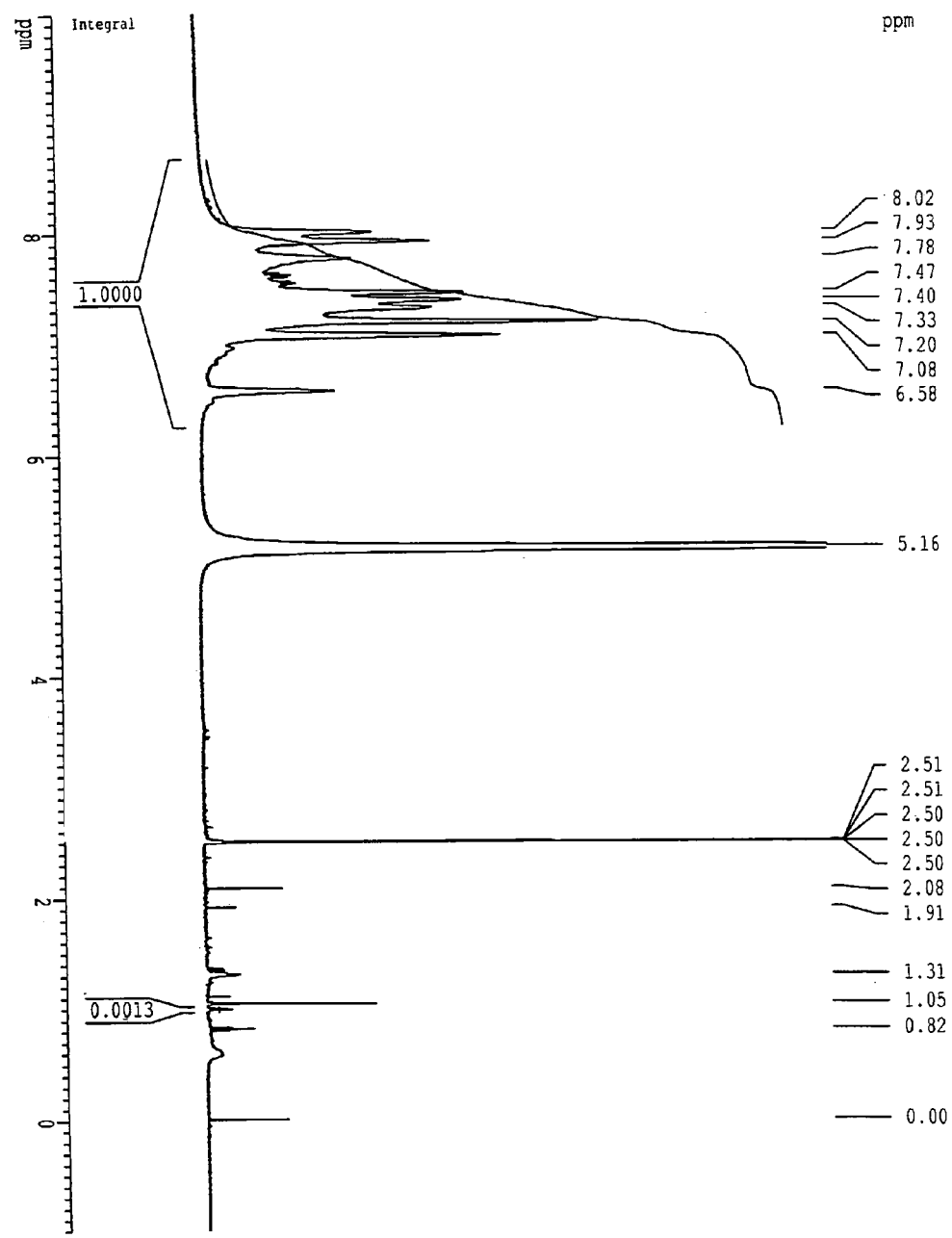
FIG. 4 is an NMR spectrum of the sulfonated polymer obtained in Example 6.

The solution obtained was then introduced into a 2-L three-necked flask equipped with a stirrer, a thermometer and a nitrogen inlet tube, and heated to 115° C. with stirring. Subsequently, 98.8 g (1140 mmol) of lithium bromide was added. After the mixture had been stirred for 7 hours, it was poured into 5 L of aceton to precipitate the product. The product was then washed sequentially with 1N hydrochloric acid and with pure water, and dried to give 223 g of a desired polymer. The weight-average molecular weight (Mw) of the polymer was 142,000. $^1$H-NMR spectrum of the polymer is shown in FIG. 4. This polymer is assumed to be a sulfonated polymer represented by the formula (IV):

An 8 wt % solution of the sulfonated polymer in NMP was cast over a glass plate to form a coating. The coating was air dried and then vacuum dried to give a film having a dry thickness of 40 μm. The film was evaluated by the above methods. The results are shown in Table 1.

TABLE 1

| Evaluation item | Unit | Ex. 2 | Ex. 4 | Ex. 6 |
|---|---|---|---|---|
| Ion exchange capacity | meq/g | 2.41 | 2.43 | 2.58 |
| Proton conductivity | S/cm | 0.31 | 0.37 | 0.36 |
| Thermal decomposition initiation temperature | ° C. | 250 | 250 | 250 |
| Hot water resistance (weight retention) | % | 100 | 100 | 100 |
| Fenton's reagent resistance (weight retention) | % | 100 | 100 | 100 |

A block copolymer composed of hydrophilic blocks and hydrophobic blocks is obtained by copolymerization of hydrophobic units of the formula (1) that have nitrile groups in the repeating units, with units of the formula (2) that have sulfonic groups in the repeating units. This copolymer is capable of giving a polymer electrolyte with excellent properties such as ion exchange capacity, proton conductivity, hot water resistance and radical resistance.

Example 7

Synthesis of Hydrophobic Units

A 1-L three-necked flask equipped with a stirrer, a thermometer, a Dean-stark tube, a nitrogen inlet tube and a cooling tube, was charged with 24.1 g (71.7 mmol) of 2,2-bis(4-hydroxyphenyl)-1,1,1,3,3,3-hexafluoropropane, 10.1 g (28.7 mmol) of 9,9-bis(4-hydroxyphenyl)fluorene, 19.7 g (115 mmol) of 2,6-dichlorobenzonitrile, and 18.0g (130 mmol) of potassium carbonate. After the flask had been purged with nitrogen, 135 mL of sulfolane and 67 mL of toluene were added, followed by stirring. The reaction liquid was heated at 150° C. under reflux in an oil bath. Water resulting from the reaction was trapped in the Dean-stark tube. Water almost ceased to occur in 3 hours, and the toluene was removed outside the reaction system through the Dean-stark tube. Subsequently, the reaction temperature was slowly raised to 200° C. and stirring was performed for

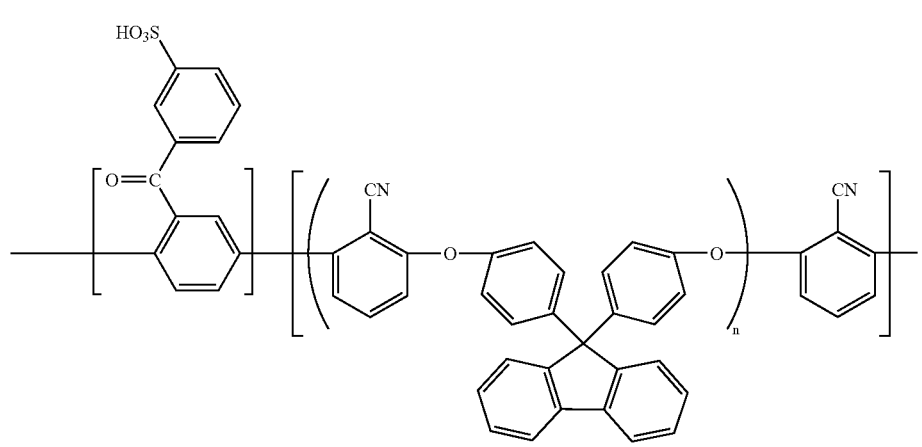

(IV)

5 hours. Thereafter, 9.86 g (57.3 mmol) of 2,6-dichlorobenzonitrile was added to carry out reaction for 3 hours.

Figure 5:
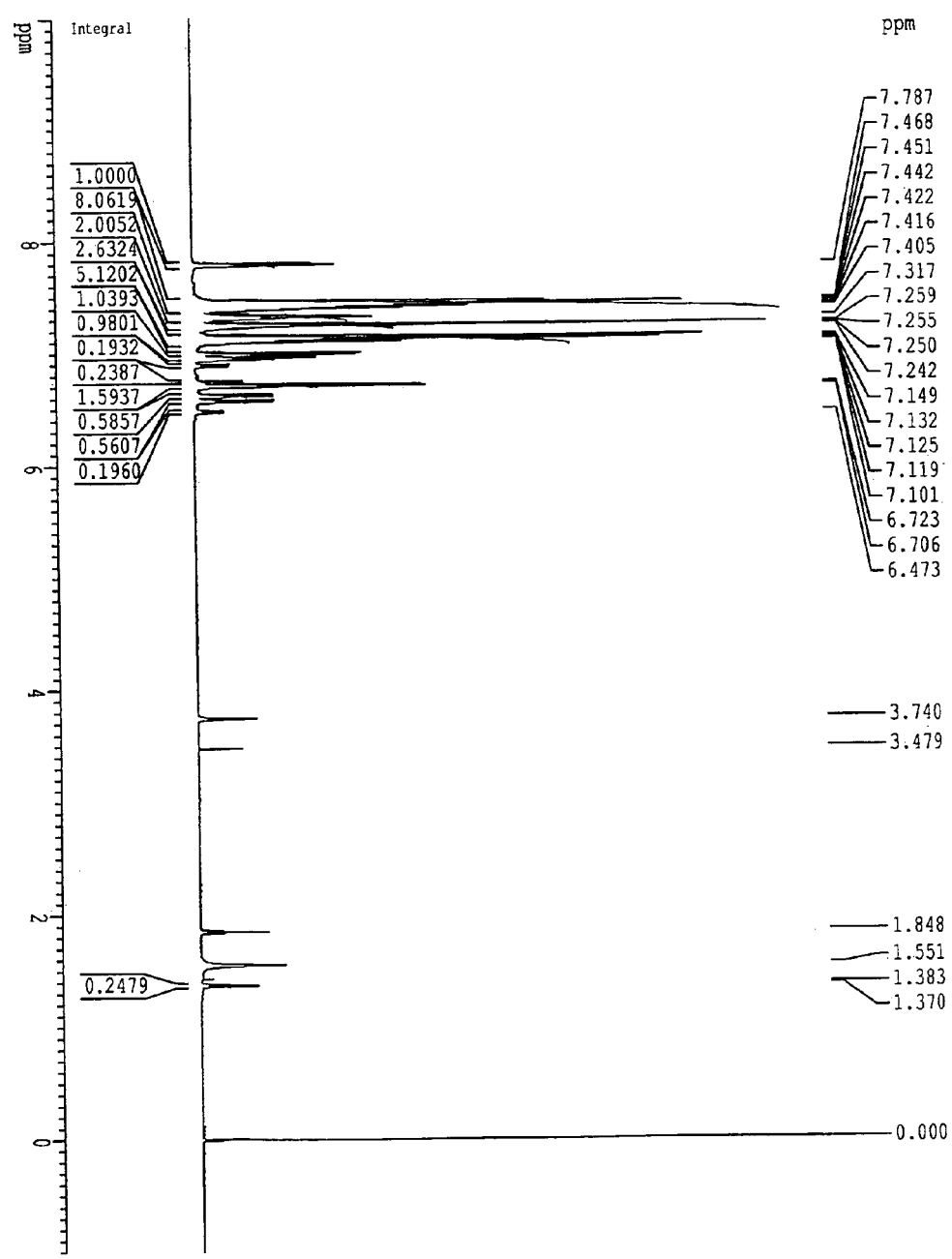
FIG. 5 is an NMR spectrum of the hydrophobic unit obtained in Example 7.

After the reaction liquid had been cooled naturally, it was diluted with 100 mL of toluene. The reaction liquid was then filtered to remove insoluble inorganic salts, and the filtrate was poured into 2 L of methanol to precipitate the product. The precipitated product was filtered off, dried and dissolved in 250 mL of tetrahydrofuran. The thus-formed solution was poured into 2 L of methanol to perform reprecipitation. The precipitated white powder was filtered off and dried to yield 40.1 g of hydrophobic units. GPC provided a number-average molecular weight (Mn) of 7400. $^1$H-NMR spectrum of the compound is shown in FIG. 5. This compound was confirmed to be an oligomer of the formula (V):

(4.2 mmol) of the Mn-7400 hydrophobic units obtained in Example 7, 5.89 g (9.0 mmol) of bis(triphenylphosphine) nickel dichloride, 1.35 g (9.0 mmol) of sodium iodide, 31.5 g (120 mmol) of triphenylphosphine, and 47.1 g (720 mmol) of zinc. After the flask had been purged with dry nitrogen, 350 mL of N,N-dimethylacetamide (DMAc) was added and the mixture was stirred for 3 hours while maintaining the reaction temperature at 80° C. The reaction liquid was diluted with 700 mL of DMAc, and insolubles were filtered.

The solution obtained was then introduced into a 2-L flask equipped with a stirrer, a thermometer and a nitrogen inlet

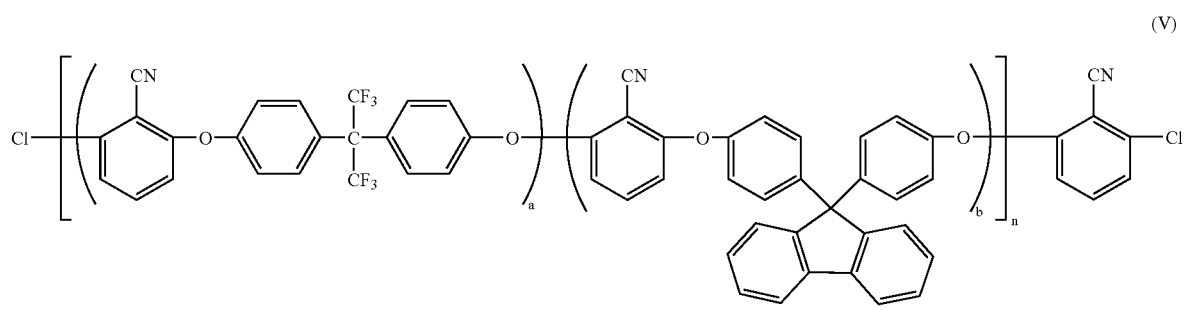

(V)

In the formula (V), the a:b ratio was 71:29. The structural units indicated with the repeating numbers a and b will be hereinafter referred to as components a and b respectively.

Example 8

Synthesis of Sulfonated Polymer

Figure 6:
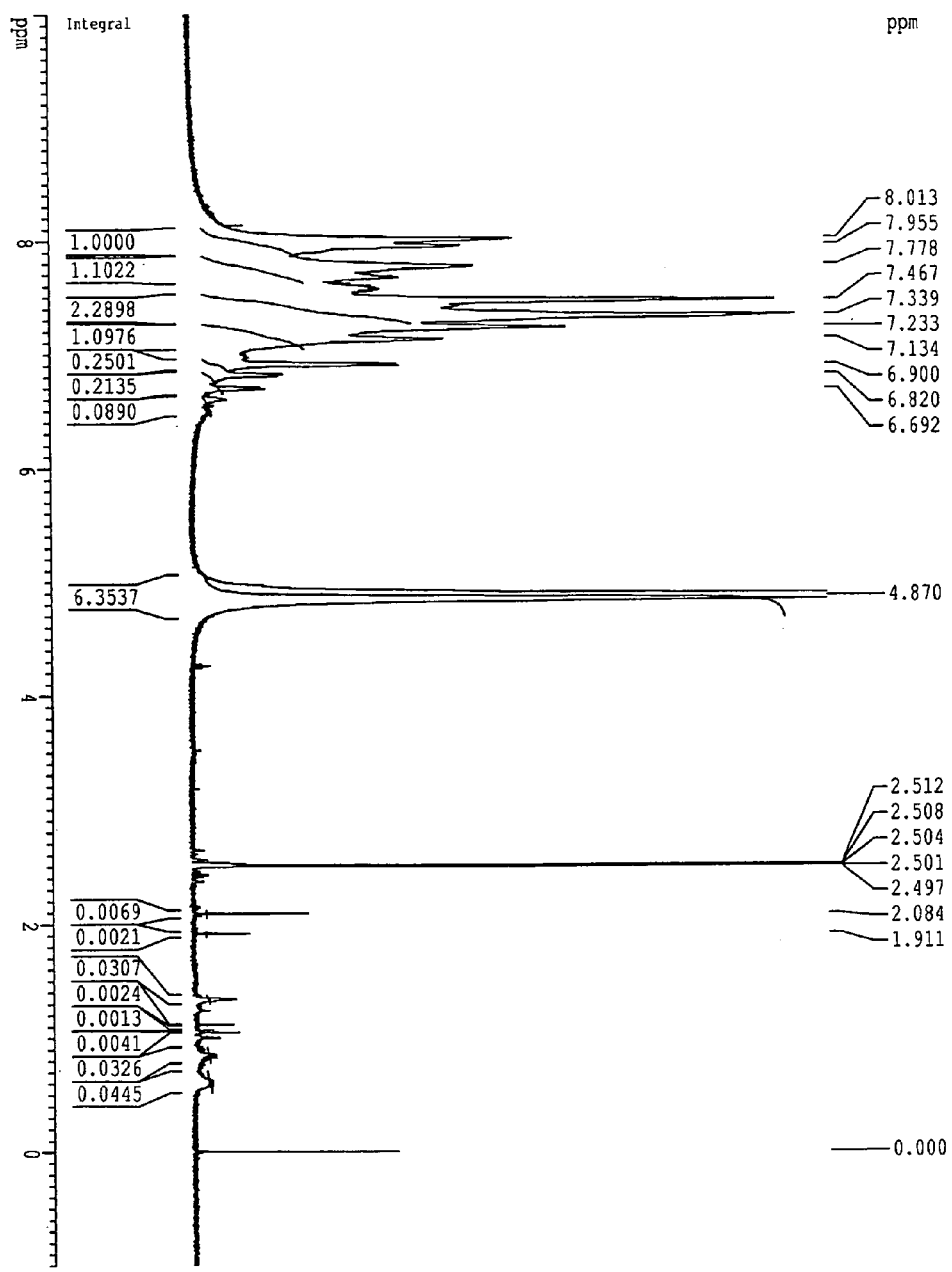
FIG. 6 is an NMR spectrum of the sulfonated polymer obtained in Example 8.

A 1-L flask equipped with a stirrer, a thermometer and a nitrogen inlet tube was charged with 119 g (296 mmol) of neopentyl 3-(2,5-dichlorobenzoyl)benzenesulfonate, 31.1 g tube, and heated to 115° C. with stirring. Subsequently, 56.5 g (651 mmol) of lithium bromide was added. After the mixture had been stirred for 7 hours, it was poured into 5 L of aceton to precipitate the product. The product was then washed sequentially with 1N hydrochloric acid and with pure water, and dried to give 102 g of an objective sulfonated polymer. The weight-average molecular weight (Mw) of the polymer was 160,000. $^1$H-NMR spectrum of the polymer is shown in FIG. 6. This polymer is assumed to be a sulfonated polymer represented by the formula (VI):

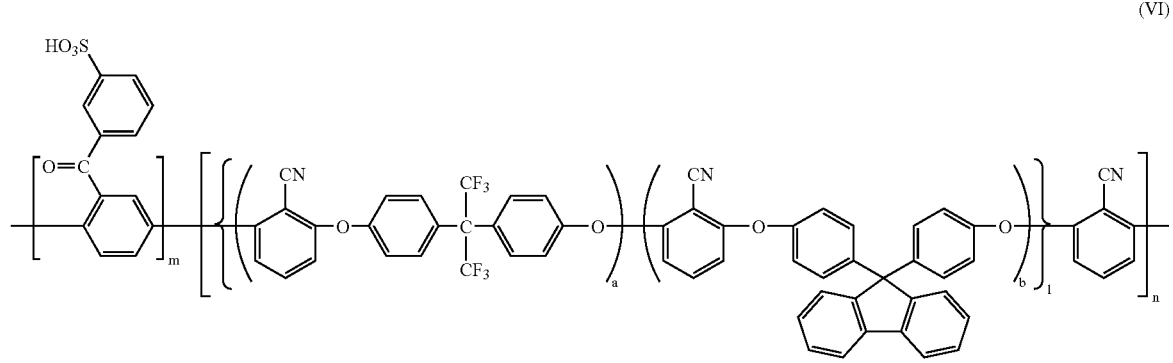

(VI)

A 10 wt % solution of the sulfonated polymer in N-methylpyrrolidone (NMP) was cast over a glass plate to form a coating. The coating was dried to give a film having a thickness of 40 μm.

Example 9

Synthesis of Hydrophobic Units

A 1-L three-necked flask equipped with a stirrer, a thermometer, a Dean-stark tube, a nitrogen inlet tube and a cooling tube, was charged with 27.8 g (82.9 mmol) of 2,2-bis(4-hydroxyphenyl)-1,1,1,3,3,3-hexafluoropropane, 3.08 g (16.5 mmol) of 4,4'-biphenol, 19.9 g (116 mmol) of 2,6-dichlorobenzonitrile, and 17.8 g (129 mmol) of potassium carbonate. After the flask had been purged with nitrogen, 130 mL of sulfolane and 63 mL of toluene were added, followed by stirring. The reaction liquid was heated at 150° C. under reflux in an oil bath. Water resulting from the reaction was trapped in the Dean-stark tube. Water almost ceased to occur in 3 hours, and the toluene was removed outside the reaction system through the Dean-stark tube. Subsequently, the reaction temperature was slowly raised to 200° C. and stirring was performed for 5 hours. Thereafter, 11.4 g (66.2 mmol) of 2,6-dichlorobenzonitrile was added to carry out reaction for 3 hours.

Figure 7:
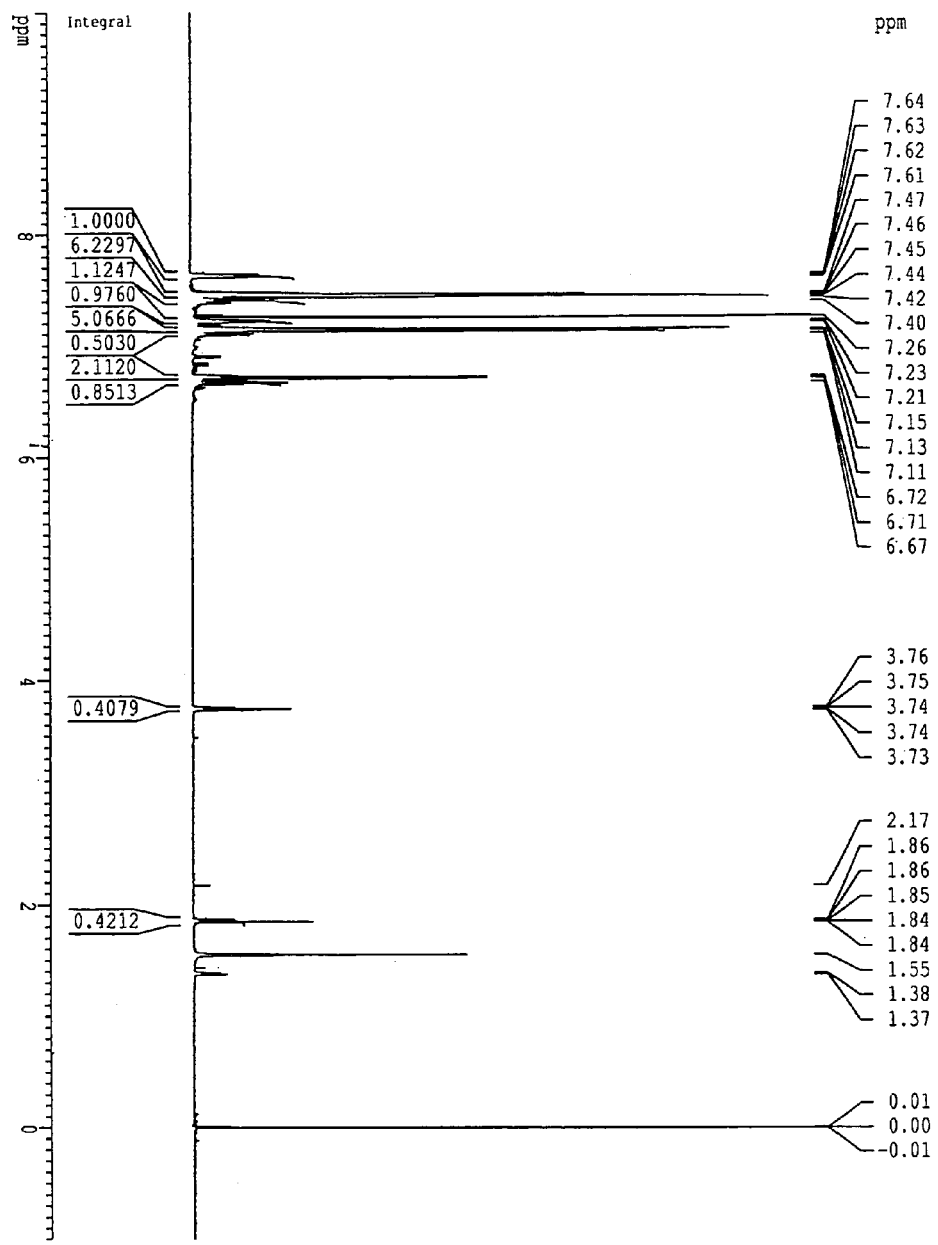
FIG. 7 is an NMR spectrum of the hydrophobic unit obtained in Example 9.

After the reaction liquid had been cooled naturally, it was diluted with 100 mL of toluene. The reaction liquid was then filtered to remove insoluble inorganic salts, and the filtrate was poured into 2 L of methanol to precipitate the product. The precipitated product was filtered off, dried and dissolved in 250 mL of tetrahydrofuran. The thus-formed solution was poured into 2 L of methanol to perform reprecipitation. The precipitated white powder was filtered off and dried to yield 39.2 g of hydrophobic units. GPC provided a number-average molecular weight (Mn) of 6000. $^1$H-NMR spectrum of the compound is shown in FIG. 7. This compound was confirmed to be an oligomer of the formula (VII):

In the formula (VII), the a:b ratio was 83:17.

Example 10

Synthesis of Sulfonated Polymer

A 1-L flask equipped with a stirrer, a thermometer and a nitrogen inlet tube was charged with 118 g (295 mmol) of neopentyl 3-(2,5-dichlorobenzoyl)benzenesulfonate, 31.5 g (5.3 mmol) of the Mn-6000 hydrophobic units obtained in Example 9, 5.89 g (9.0 mmol) of bis(triphenylphosphine) nickel dichloride, 1.35 g (9.0 mmol) of sodium iodide, 31.5 g (120 mmol) of triphenylphosphine, and 47.1 g (720 mmol) of zinc. After the flask had been purged with dry nitrogen, 350 mL of N,N-dimethylacetamide (DMAc) was added and the mixture was stirred for 3 hours while maintaining the reaction temperature at 80° C. The reaction liquid was diluted with 700 mL of DMAc, and insolubles were filtered.

Figure 8:
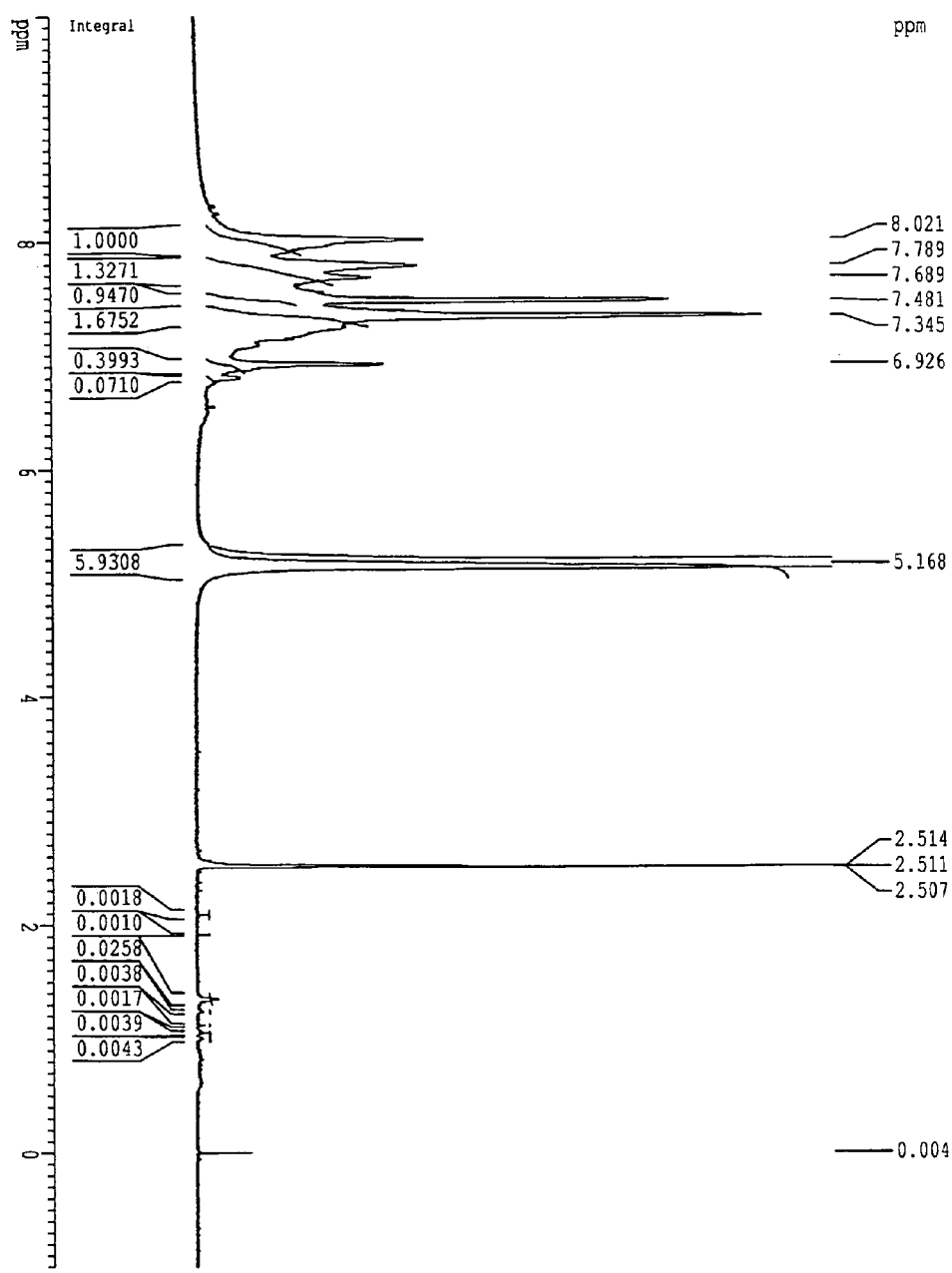
FIG. 8 is an NMR spectrum of the sulfonated polymer obtained in Example 10.

The solution obtained was then introduced into a 2-L flask equipped with a stirrer, a thermometer and a nitrogen inlet tube, and heated to 115° C. with stirring. Subsequently, 56.3 g (648 mmol) of lithium bromide was added. After the mixture had been stirred for 7 hours, it was poured into 5 L of aceton to precipitate the product. The product was then washed sequentially with 1N hydrochloric acid and with pure water, and dried to give 101 g of an objective sulfonated polymer. The weight-average molecular weight (Mw) of the polymer was 165,000. $^1$H-NMR spectrum of the polymer is shown in FIG. 8. This polymer is assumed to be a sulfonated polymer represented by the formula (VIII):

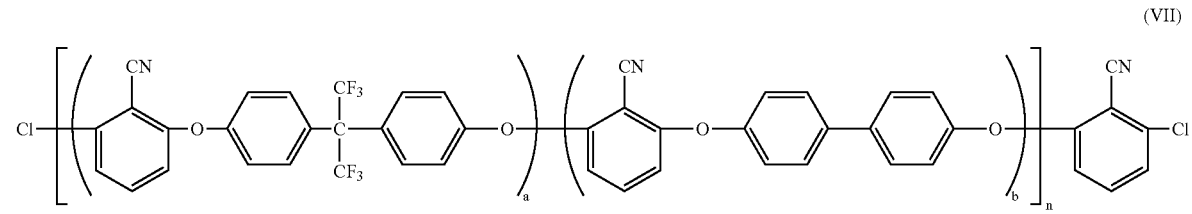

(VII)

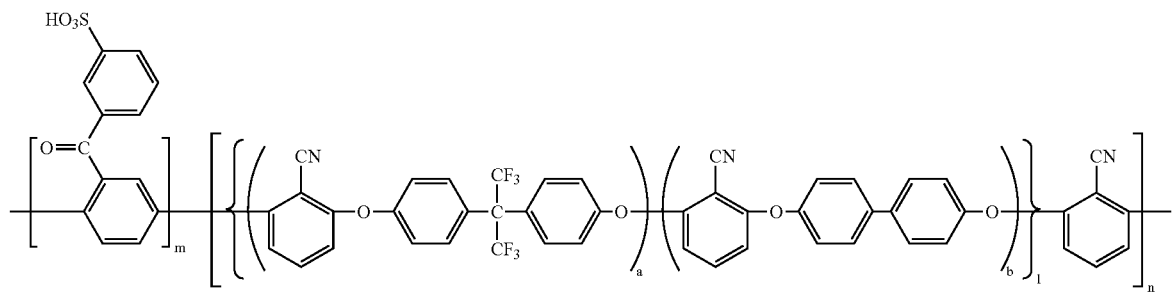

(VIII)

A 10 wt % solution of the sulfonated polymer in N-methylpyrrolidone (NMP) was cast over a glass plate to form a coating. The coating was dried to give a film having a thickness of 40 μm.

[Evaluation]

The sulfonated polymers and films (proton conductive membranes) obtained in Examples 8 and 10 were tested by the aforesaid methods to evaluate the properties. After the hot water resistant test, the films were measured for size, and the dimensional changes of the tested films relative to the original size were determined. The results are shown in Table 2.

TABLE 2

|  |  | Example | |
|---|---|---|---|
|  |  | 8 | 10 |
| Composition | Component a | 71 | 83 |
|  | Component b | 29 | 17 |
| Ion exchange capacity | (meq/g) | 2.6 | 2.6 |
| Proton conductivity | (S/cm) | 0.41 | 0.43 |
| Hot water resistance | % (weight retention) | 100 | 100 |
|  | % (dimensional change) | 120 | 124 |

The invention claimed is:

1. A compound represented by the formula (1):

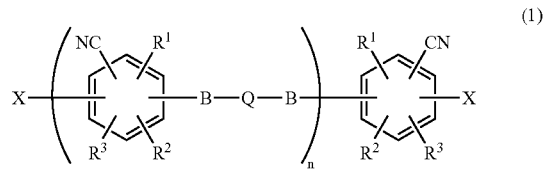

(1)

wherein B's are each independently an oxygen or a sulfur atom, X's are each an atom or a group selected from halogen atoms other than fluorine, —OSO$_2$CH$_3$ and —OSO$_2$CF$_3$, $R^1$ to $R^3$ may be the same or different and are selected from a hydrogen atom, a fluorine atom, a nitrile group and an alkyl group, n is an integer of 2 or greater, and Q is a structure represented by the formula (q):

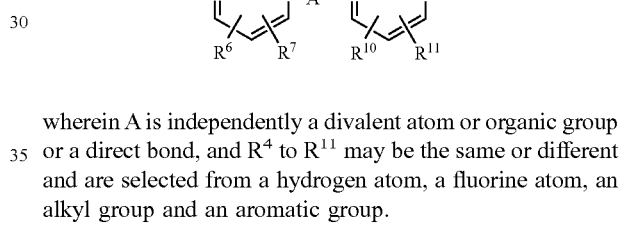

(q)

wherein A is independently a divalent atom or organic group or a direct bond, and $R^4$ to $R^{11}$ may be the same or different and are selected from a hydrogen atom, a fluorine atom, an alkyl group and an aromatic group.

2. The compound as claimed in claim 1, wherein A in the structure represented by the formula (q) is a direct bond or an organic group selected from —CONH—, —(CF$_2$)$_p$— (wherein p is an integer of 1 to 10), —C(CF$_3$)$_2$—, —COO—, —SO—, —SO$_2$— and a group represented by the formula (a):

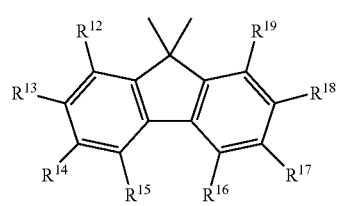

(a)

wherein $R^{12}$ to $R^{19}$ may be the same or different and are each a hydrogen atom, a fluorine atom, an alkyl group or an aromatic group.

3. The compound as claimed in claim 1, comprising a structure (Q1) represented by the formula (q) in which A is an organic group selected from —CONH—, —(CF$_2$)$_p$— (wherein p is an integer of 1 to 10), —C(CF$_3$)$_2$—, —COO—, —SO— and —SO$_2$—, and a structure (Q2) of the same formula in which A is a direct bond or a group represented by the formula (a):

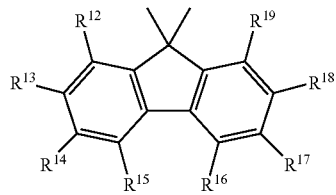

wherein $R^{12}$ to $R^{19}$ may be the same or different and are each a hydrogen atom, a fluorine atom, an alkyl group or an aromatic group.

4. The compound as claimed in claim 3, wherein the structure (Q1) accounts for 99 to 20 mol % and the structure (Q2) accounts for 1 to 80 mol % (with the proviso that the total of the structures (Q1) and (Q2) is 100 mol %).

5. A polyarylene polymer comprising repeating units represented by the formula (1'):

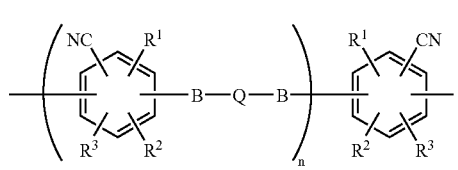

wherein B's are each independently an oxygen or a sulfur atom, $R^1$ to $R^3$ may be the same or different and are selected from a hydrogen atom, a fluorine atom, a nitrile group and an alkyl group, n is an integer of 2 or greater, and Q is a structure represented by the formula (q):

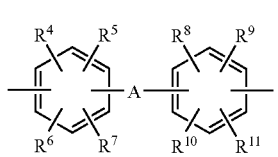

wherein A is independently a divalent atom or organic group or a direct bond, and $R^4$ to $R^{11}$ may be the same or different and are selected from a hydrogen atom, a fluorine atom, an alkyl group and an aromatic group.

6. The polyarylene polymer as claimed in claim 5, wherein A in the structure represented by the formula (q) is a direct bond or an organic group selected from —CONH—, —(CF$_2$)$_p$— (wherein p is an integer of 1 to 10), —C(CF$_3$)$_2$—, —COO—, —SO—, —SO$_2$— and a group represented by the formula (a):

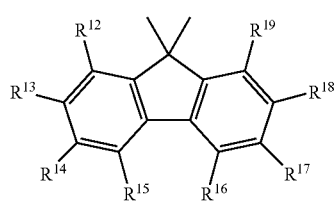

wherein $R^{12}$ to $R^{19}$ may be the same or different and are each a hydrogen atom, a fluorine atom, an alkyl group or an aromatic group.

7. The polyarylene polymer as claimed in claim 5, comprising a structure (Q1) represented by the formula (q) in which A is an organic group selected from —CONH—, —(CF$_2$)$_p$— (wherein p is an integer of 1 to 10), —C(CF$_3$)$_2$—, —COO—, —SO— and —SO$_2$—, and a structure (Q2) of the same formula in which A is a direct bond or a group represented by the formula (a):

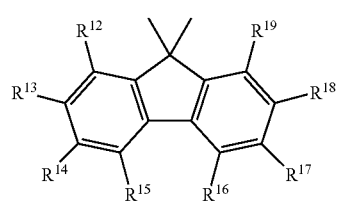

wherein $R^{12}$ to $R^{19}$ may be the same or different and are each a hydrogen atom, a fluorine atom, an alkyl group or an aromatic group.

8. The polyarylene polymer as claimed in claim 7, wherein the structure (Q1) accounts for 99 to 20 mol % and the structure (Q2) accounts for 1 to 80 mol % (with the proviso that the total of the structures (Q1) and (Q2) is 100 mol %).

9. The polyarylene polymer as claimed in claim 5, comprising repeating units of the formula (2) shown below:

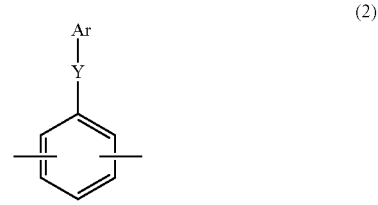

wherein Y is a divalent atom or organic group or a direct bond, and Ar is an aromatic group.

10. The polyarylene polymer as claimed in claim 9, wherein the repeating units of the formula (2) have a sulfonate group.

11. The polyarylene polymer as claimed in claim 9, wherein the repeating units of the formula (2) have a sulfonic group.

12. A solid polymer electrolyte comprising the polyarylene polymer having a sulfonic group described in claim 11.

13. A proton conductive membrane comprising the polyarylene polymer having a sulfonic group described in claim 11.

* * * * *